United States Patent
Pertejo et al.

(10) Patent No.: US 8,759,485 B2
(45) Date of Patent: Jun. 24, 2014

(54) CHEMOKINE BINDING ACTIVITY OF VIRAL TNF RECEPTORS AND RELATED PROTEINS

(75) Inventors: Antonio Alcami Alcami Pertejo, San Sebastian de Reyes (ES); Ali Alejo Herberg, Madrid (ES); Maria Begona Ruiz-Arguello, Berango (ES); Yin Ho, Cambridge (GB); Margarida Saraiva, Matosinhos (PT); Vincent P. Smith, Cambridge (GB)

(73) Assignee: Antonio Alcami Pertejo, Sebastian de Reyes (ES)

( * ) Notice: Subject to any disclaimer, the term of this patent is extended or adjusted under 35 U.S.C. 154(b) by 531 days.

(21) Appl. No.: 11/661,633

(22) PCT Filed: Sep. 2, 2005

(86) PCT No.: PCT/EP2005/009449
§ 371 (c)(1),
(2), (4) Date: Mar. 1, 2007

(87) PCT Pub. No.: WO2006/024533
PCT Pub. Date: Mar. 9, 2006

(65) Prior Publication Data
US 2009/0104178 A1 Apr. 23, 2009

(30) Foreign Application Priority Data
Sep. 2, 2004 (ES) .................................. 200402123

(51) Int. Cl.
C07K 1/00 (2006.01)
C07K 14/00 (2006.01)
C12P 21/04 (2006.01)
A61K 38/00 (2006.01)
A61K 38/16 (2006.01)
A61K 39/00 (2006.01)

(52) U.S. Cl.
USPC ......... 530/351; 530/350; 435/69.7; 514/20.6; 514/21.2; 424/185.1; 424/192.1

(58) Field of Classification Search
None
See application file for complete search history.

(56) References Cited

U.S. PATENT DOCUMENTS 5,464,938 A 11/1995 Smith et al.
7,186,408 B2 * 3/2007 Alcami et al. ............... 424/93.1

FOREIGN PATENT DOCUMENTS

WO  WO-98/36766 A  8/1998
WO  WO-00/71150 A  11/2000

OTHER PUBLICATIONS

Record for Accession No. Q8QMN0; NCBI Protein Database; created Jun. 1, 2002. 2 pages as printed.*
Alejo et al (2006. PNAS. 103(15): 5995-6000).*
Ngo et al., 1994, Computational Complexity, Protein Structure prediction, and the Levinthal Paradox, The Protein Folding Problem and Tertiary Structure Prediction, pp. 492-495.*
Wells, Aditivity of Mutational Effects in Proteins, 1990, Biochemistry, vol. 26, No. 37, pp. 8509-8517.*
Ribas et. al. Genetic Variability of Immunomodulatory Genes in Ectromelia Virus Isolates Detected by Denaturing high-Performance Liquid Chromatography, J.ournal of Virology, vol. 77, No. 18

(56) References Cited

OTHER PUBLICATIONS

Hu, etal, (1994). Cowpox virus contains two copies of an early gene encoding a soluble secreted form of the type II TNF receptor. Virology, vol. 204, 343-356.

Johnston, et al, (2004). Technical knockout: understanding poxvirus pathogenesis by selectively deleting viral immunomodulatory gene., Cell Microbiol vol. 6, 695-705.

Lalani, et al. (1997). The purfied myxoma virus gamma interferon receptor homolog MT7 interacts with the heparin-binding domains of chemokines. J. Virol, vol. 71, 4356-63.

Lalani, A. S., Masters, J., Graham, K., Liu, L., Lucas, A. & McFadden, G. (1999). Role of the myxoma virus soluble CC-chemokine inhibitor myxoma virus pathogenesis. Virology 256, 233-45.

Lalani, A. S., Ness, T. L., Singh, R., Harrison, J. K., Seet, B. T., Kelvin, D. J., McFadden, 5 G. & Moyer, R. W. 998). Functional comparisons among members of the family of soluble CC-chemokine inhibitor glycoproteins. Virology 250, 173-84, (1998).

Locksley, R. M., N. & Lenardo, M. J. (2001). The TNF and TNF receptor superfamilies: integrating mammalian biology. Cell 104, 487-501.

Loparev, et al. (1998). A third distinct tumor necrosis factor receptor of orthopoxviruses. Proc. Natl. Acad. Sci. U.S.A. 95, 3786-3791.

Parry, et al (2000). A broad spectrum secreted chemokine binding protein 15 encoded by a herpesvirus. J. Exp. Med. 191, 573-8.

Price, N., Tscharke, D. C.. Hollinshead, M. & Smith, G. L. (2000). Vaccinia virus gene B7R encodes an protein that is resident in the endoplasmic reticulum and affects virus virulence. Virology 267, 65-79.

Reading, P. C., Symons, J. A. & Smith, G. L. (2003). A soluble chemokine-binding 20 protein from vaccinia virus reduces virus virulence and the inflammatory response to infection. J. Immunol 170, 1435-42.

Saraiva, M. etal. (2001) CrmE, a novel soluble tumor necrosis factor receptor encoded by poxviruses, J. Virol. 75, 226-33.

Schreiber,et al (1997). Distinct domains of M-T2, the 25 myxoma virus TNF receptor mediate extracellular TNF binding and intracellular apoptosis inhibition, J. Virol. 71, 2171-2181.

Seet, et al, (2003) Poxviruses and immune evasion. Annu Rev Immunol 21, 377-423.

Seet, et al (2002) Viral chemokine-binding proteins. J Leukoc Biol 72, 24-34.

Smith, et al. (1996) Cowpox virus genome encodes a second soluble homologue of cellular TNF receptors, distinct from CrmB, that binds TNF but not LT alpha. Virology 223, 132-147.

Van Berkel, et al. (2000) Identification of a gammaherpesvirus selective chemokine binding protein that inhibits chemokine action, J. Virol. 74, 6741-7.

Wallach, et al. (2001) TNF ligand and receptor families. In Reference, pp. 377-412. Edited by J. Oppenheim M. Feldman: Academic Press.

Zaballos, et al. (1999) Cutting edge: identification of the orphan chernokine receptor GPR-9-6 as CCR9, the receptor for the chemokine TECK. J Immunol 162, 5671-5.

* cited by examiner

Fig. 1

| | CrmB | CrmC | CrmD | CrmE | CTD1 | CTD2 | CTD3 |
|---|---|---|---|---|---|---|---|
| CPV Brighton Red | V005 | V191 | V221 | — | V014 | V201 | V218 |
| CPV GRI | I4R | A53R | K2R | K3R | D12L | B6R | B21R |
| EV Naval | — | — | E3 | — | E12 | E184 | — |
| VaV Bangladesh | G2R | — | — | — | — | — | — |
| VV Western Reserve | — | — | — | — | — | VACWR188 (B7R) | VACWR206 |

CLUSTAL W (1.82) multiple sequence alignment

```
CrmDCPV    -MMNMTPSYILLVYMFVVVSGDVP-YEHINGKCNGTDYNSNNLCCKQCDPGMYMTHSCNT  58
CrmDEV     -MMKMTPSYILLVYMFVVVSGDVP-YTPINGKCNGTDYNSNNLCCKQCNPGMYMTHSCNT  58
CrmBVaV    -MKSVLYLYILFLSCIING-RDAAPYTPPNGKCKDTEYKRHNLCCLSCPPGTYASRLCDS  58
CrmBCPV    -MKS--YILLLLSCIIINSDITPHEPSNGKCKDNEYKRHHLCCLSCPPGTYASRLCDS    57
E12EV      -MININITILIFASLFVA---------------SFANDYP------PPGFFENKYITD    37
E12CPV     -MININITILIFASLFVA---------------SFANDYP------PPGFFEDKYITN    37
B7RVV      -MYKKLITFLFVIGALASY--------------SNNEYT-------------------    24
B7REV      -MYKKLITFLFVIGAVASY--------------SNNEYT-------------------    24
B21RCPV    MMIYGLIACLIFVTSSIASPLYIP-------VIPPITEDK------------------    33
B21RVV     MMIYGLIACLIFVTSSIASPLYIP-------VIPPISEDK------------------    33
              *          :::.                  :.:

CrmDCPV    TSNT--KCDKCPDGTFTSIPNHIPTCLSCRGKCSSNHVETKSCSNTQDRVCVCASGYYCE  116
CrmDEV     TSNT--KCDKCPDDTFTSIPNHSPACLSCRGKCSSNQVETKSCSNTQDRVCVCASGYYCE  116
CrmBVaV    KTNT--QCTPCGSGTFTSRNNHLPACLSCNGRCNSNQVETRSCNTTHNRICECSPGYYCL  116
CrmBCPV    KTNTNTNTQCTPCASDTFTSRNNHLPACLSCNGRCDSNQVETRSCNTTHNRICDCAPGYYCF  117
E12EV      --------------------------------------------------------
E12CPV     --------------------------------------------------------
B7RVV      --------------------------------------------------------
B7REV      --------------------------------------------------------
B21RCPV    --------------------------------------------------------
B21RVV     --------------------------------------------------------
```

Figure 2B

```
CrmDCPV   FEGSNGCRLCVPQTKCDSGYGVYGYSSKGDVICKKC------------PGNIDKCD----LSFN   164
CrmDEV    FEGSNGCRLCVPQTKCDSGYGVYGYSSKGDVICKKC------------PGNIDKCD----LSFN   164
CrmBVaV   LKGSSGCKACVSQTKCGIGYGVSGHTSVGDVICSPCGFGTYSHTVSSADKCEPVPNNTFN        176
CrmBCPV   LKGSSGCKACVSQTKCGIGYGVSGHTPTGDVVCSPCGLGTYSHTVSSVDKCEPVPSNTFN        177
E12EV     --------------------------------------------------------TFN         40
E12CPV    --------------------------------------------------------TFN         40
B7RVV     --------------------------------------------------------PFN         27
B7REV     --------------------------------------------------------PFN         27
B21RCPV   --------------------------------------------------------SFN         36
B21RVV    --------------------------------------------------------SFN         36
                                                                 **

CrmDCPV   SIDVEINMYPVNKTSCN--SSIGSSSTISTSELTITLKHEDCTTVFIGDYYSVVDKLATS        222
CrmDEV    SIDVEINMYPVNKTSCN--SSIGSSSTISTSELTITLTHEDCTPVFIGDYYSVVDKLATS        222
CrmBVaV   YIDVEITLYPVNDTSCTRTTTGLSESILTSELTITMNHTDCNPVFREEYFSVLNKVATS         236
CrmBCPV   YIDVEINLYPVNDTSCTRTTTGLSESISTSELTITMNHKDCDPVFRNGYFSVLNEVATS         237
E12EV     YISIDFELYPVNVSSCNRLSTKQSSDIITTSELTITVNSTDCDPVFVTEYYSVKDKTAVA        100
E12CPV    YISIDFELYPVNVSSCNRLSTKQSSDVISTSELTITVNSTDCDPVFVTEYYSVKDKTAIA        100
B7RVV     KLSVKLYIDGVDNIENS--YTDDNNELVLNFKEYTISIITESCDVGFDSIDIDVINDYKII        86
B7REV     KLSVKLYIDGVDNIENS--YTD-NNELVLNFKEYTISIITESCDVGFDSIDIDVINDYKIL       85
B21RCPV   SVEVLVSLFRDEQKDYT--VTSQFNNYTIDTKDWTINVLSTPDGLEIPLTNITYWSRFPTI       95
B21RVV    SVEVLVSLFRDDQKDYT--VTSQFNNYTIDTKDWTIGVLSTPDGLDIPLTNITYWSRF-TI       94
                          **         ..                   .                  .
```

Figure 2C

```
CrmDCPV     GFFTNDK---VHQDLTTQCKINLEIKCNSGG-----ESRQLTPTTKVY--FMPHSETVTVVGD 275
CrmDEV      GFFTNDK---VHQDLTTQCKINLEIKCNSGR-----ESRQLTPTTKVY--LMPHSETVTVVGD 275
CrmBVaV     GFFTGEN---RYQNISKVCTLNFEIKCNNKG---SSFKQLTKAKNDD-GMMSHSETVTLAGD 291
CrmBCPV     GFFTGQN---RYQNISKVCTLNFEIKCNNKDSYSSSKQLTKTKNDDDSIMPHSESVTLVGD 295
E12EV       GLFTDTT---KKQNTSKMCTLNVEVKCNAET-----EPVLIGNFTRVPETASTHAENFTLIGN 155
E12CPV      GLFTDTT---KKQNTSKMCTLNIEVKCNAET-----EPVLIGNFTRVPEKASTHAENFTLIGN 155
B7RVV       DMYTIDSS-TIQRRGHTCRISTKLSCHYDK------YPYIHKYDGDE-----RQYSITAEGK 136
B7REV       DMYTIDSS-TIQRRGHTCKISTKLSCHYDK------HPYIHKYEGDE-----RQYSITAEGK 135
B21RCPV     GHALFKSESEDIFQKNMSILGVSIECKKPS---TSFTFLTVRKISRVFNRFPDMAYYRGD 152
B21RVV      GRALFKSESEDIFQKKMSILGVSIECKKSS---TLLTFLTVRKMTRVFNKFPDMAYYRGD 151
                  .  :  :  :*::       .         :                  *.

CrmDCPV     CLSNLDVYIVYANTDAIYSDMDVVAYHTSYILNVDHIPPNDCERD-------------- 320
CrmDEV      CLSNLDVYIVYANTDAIYSDMDVVAYHTSYILNVDHIPPNDCERD-------------- 320
CrmBVaV     CLSSVDIYILYSNTNAQDYETDTISYRVGNVLDDDSHMPGSCNIHKPITNSK----PTRFL 348
CrmBCPV     CLSSVDIYILYSNTNTQDYETDTISYHVGNVLDVDSHMPGRCDTHKLITNSNSQYPTHFL 355
E12EV       CLSDLHLYIAYVNTDEG--FEEDTATIHIGNMIDISGIPPNTCATRTIN---------- 202
E12CPV      CLSDLHLYIAYVNTDEE--FEEDTATVHIGNKLDINGIPPNMCATRTIN---------- 202
B7RVV       CYKGIKYEISMIN-DDTLLRKHTLKIGSTYIFDRHGHSNTYYSKYDF------------ 182
B7REV       CYKGIKYEISMH-DDTLLRKHTLKIGSTYIFDRHGHSNTYYSKYDF------------- 181
B21RCPV     CLEVVYVTMTYKNTKTG--ETDYTYLSNVGIPEYYRLMSGVDG--------------- 193
B21RVV      CLKAVYVTMTYKNTKTG--ETDYTYLSNGGLPAYYR--NGVDG--------------- 190
             *    .    :   ::   .     .
```

Figure 2D

CLUSTAL W (1.82) multiple sequence alignment (CrmB / CrmD)

```
CrmBVaV    MKSVLYLYILFLSCIING-RDAAPYTPPNGKCKDTEYKRHNLCCLSCPPGTYASRLCDSK   59
CrmBCPV    MKS--YILLLLLSCIIINSDITPHEPSNGKCKDNEYKRHHLCCLSCPPGTYASRLCDSK   58
CrmDCPV    MMNMTPSYILLVYMFVVVSGDVP-YEHINGKCNGTDYNSNNLCCKQCDPGMYMTHSCNTT   59
CrmDEV     MMKMTPSYILLVYMFVVVSGDVP-YTPINGKCNGTDYNSNNLCCKQCNPGMYMTHSCNTT   59
               :  :*:: ::         *   .  .       ****:..:.*: ::.****  *:.*   *:..

CrmBVaV    TNT--QCTPCGSGTFTSRNNHLPACLSCNGRCNSNQVETRSCNTTHNRICECSPGYYCLL  117
CrmBCPV    TNTNTQCTPCASDTFTSRNNHLPACLSCNGRCDSNQVETRSCNTTHNRICDCAPGYYCFL  118
CrmDCPV    SNT--KCDKCPDGTFTSIPNHIPTCLSCRGKCSSNHVETKSCSNTQDRVCVCASGYYCEF  117
CrmDEV     SNT--KCDKCPDDTFTSIPNHSPACLSCRGKCSRGKCSSNQVETKSCSNTQDRVCVCASGYYCEF  117
           :**     :*  *   .:****  ** *::****  **  *: ***. .*::*:.* *::::** .*:.****  :

CrmBVaV    KGSSGCKACVSQTKCGIGYGVSGHTSVGDVICSPCGFGTYSHTVSSADKCEPVPNNTFNY  177
CrmBCPV    KGSSGCKACVSQTKCGIGYGVSGHTPTGDVVCSPCGLGTYSHTVSSVDKCEPVPSNTFNY  178
CrmDCPV    EGSNGCRLCVPQTKCDSGYGVYGYSSKGDVICKKC------PGNIDKCD----LSFNS  165
CrmDEV     EGSNGCRLCVPQTKCGSGYGVYGYSSKGDVICKKC------PGNIDKCD----LSFNS  165
           :**.**:.* ** ****  . *** ****  **:*:. ***:*:.* *     :..  :**

CrmBVaV    IDVEITLYPVNDTSCTRTTTTGLSESILTSELTITMNHTDCNPVFREEYFSVLNKVATSG  237
CrmBCPV    IDVEINLYPVNDTSCTRTTTTGLSESISTSELTITMNHKDCDPVFRNGYFSVLNEVATSG  238
CrmDCPV    IDVEINMYPVNKTSCN--SSIGSSTISTSELTITLKHEDCTTVFIGDYYSVVDKLATSG  223
CrmDEV     IDVEINMYPVNKTSCN--SSIGSSTISTSELTITLTHEDCTPVFIGDYYSVVDKLATSG  223
           *****.:.***:.***    ::* .:*  *   * ***********:..* .** .:*****
```

Figure 2E

```
CrmBVaV    FFTGENRYQNISKVCTLNFEIKCNNKG--SSFKQLTKAKNDD-GMMSHSETVTLAGDCLS 294
CrmBCPV    FFTGQNRYQNISKVCTLNFEIKCNNKDSYSSSKQLTKTKNDDDSIMPHSESVTLVGDCLS 298
CrmDCPV    FFTNDKVHQDLTTQCKINLEIKCNSGG---ESRQLTPTTKVY--FMPHSETVTVVGDCLS 278
CrmDEV     FFTNDKVHQDLTTQCKINLEIKCNSGR---ESRQLTPTTKVY--LMPHSETVTVVGDCLS 278
           ***.:: :*:::::  *.:*:******.    :**** :::    :*.****:.:*****

CrmBVaV    SVDIYILYSNTNAQDYETDTISYRVGNVLDDDSHMPGSCNIHKPITNSK---PTRFL 348
CrmBCPV    SVDIYILYSNTNTQDYETDTISYHVGNVLDVDSHMPGRCDTHKLITNSNSQYPTHFL 355
CrmDCPV    NLDVYIVYANTDAIYSDMDVVAYHTSYILNVDHIPPNDCERD--------------- 320
CrmDEV     NLDVYIVYANTDAIYSDMDVVAYHTSYILNVDHIPPNDCERD--------------- 320
           .:*:**:*.**:: .  : ..*::... .:*: *   *. **  .
```

Figure 2F

CLUSTAL W (1.82) multiple sequence alignment (CTDs)

```
E12EV    -MINININTILIFASLFVASFANDYPPPGFFENKYITDTFNYISIDFELYPVNVSSCNRL   59
E12CPV   -MINININTILIFASLFVASFANDYPPPGFFEDKYITNTFNYISIDFELYPVNVSSCNRL   59
B7RVV    --MYKKLITFLFVIGALASYSNNEYTP--------ENKLSVKLYIDGVDN-IENSY      45
B7REV    --MYKKLITFLFVIGAVASYSNNEYTP--------FNKLSVKLYIDGVDN-IENSY      45
B21RCPV  MMIYGLIACLIFVTSSTASPLYIPVIPP-----ITEDKSFNSVEVLVSLFRDEQ-KDYTV  54
B21RVV   MMIYGLIACLIFVTSSIASPLYIPVIPP-----ISEDKSFNSVEVLVSLFRDDQ-KDYTV  54
           :  :   :  :  :.: :*   . :**    .   :: . :

E12EV    STKQSSDIITTSELTITVNSTDCDPVFVTEYYSVKDKTAVAGLFT-DTTKK-QNTSKMCT  117
E12CPV   STKQSSDVISTSELTITVNSTDCDPVFVTEYYSVKDKTAIAGLFT-DTTKK-QNTSKMCT  117
B7RVV    TDDNNELVLNFKEYTISIITESCDVGFDSIDIDVINDYKIIDMYTIDSSTI-QRRGHTCR  104
B7REV    TD-NNELVLNFKEYTISIITESCDVGFDSIDIDVINDYKILDMYTIDSSTI-QRRGHTCK  103
B21RCPV  TSQFNNYTIDTKDWTINVLSTPDGLEIPLTNITYWSRFPTIGHALFKSESEDIFQKNMSI  114
B21RVV   TSQFNNYTIDTKDWTIGVLSTPDGLDIPLTNITYWSRF-TIGRALFKSESEDIFQKKMSI  113
          .   .  :   :: **  .  .    :    :.  :  .  :   .: : : ::  :

E12EV    LNVEVKCNAETEPVLIGNFTRVPETASTHAENFTLIGNCLSDLHLYIAYVNTDEGFEEDT  177
E12CPV   LNIEVKCNAETEPVLIGNFTRVPEKASTHAENFTLIGNCLSDLHLYIAYVNTDEEFEEDT  177
B7RVV    ISTKLSCHYDKYPYIH------KYDGDERQYSITAEGKCYKGIKYEISMINDDTLLRKHT  158
B7REV    ISTKLSCHYDKHPYIH------KYEGDERQYSITAEGKCYKGIKYEISMMHDDTLLRKHT  157
B21RCPV  LGVSIECKKPSTSFTELTVRKISRVFNRFPDMAYYRGDCLEVYVVTMTYKNTKTGETDYT  174
B21RVV   LGVSIECKKSSTLLTFLTVRKMTRVFNKFPDMAYYRGDCLKAVYVTMTYKNTKTGETDYT  173
          .    *   .*   . :  *:            .      *
```

Figure 2G

```
E12EV    ATIHIGNMIDISGIPPNTCATRTIN-        202
E12CPV   ATVHIGNKLDINGIPPNMCATRTIN-        202
B7RVV    LKIGSTYIFDRHGHSNTYYSKYDF---       182
B7REV    LKIGSTYIFDRHGHSNTYYSKYDF---       181
B21RCPV  YLSNV-------GIPEYYRLMSGVDG        193
B21RVV   YLSNG-------GLPAYYR--NGVDG        190
                *       .            : :
```

Fig. 5

EV CrmD binding to chemokines

| CHEMOKINE | $K_D$ (nM) |
| --- | --- |
| hCCL28 | 2.8 |
| mCCL25 | 3.2 |
| mCXCL14 | 3.2 |
| hCCL20 | 4.3 |
| hCXCL14 | 7.1 |
| hCXCL13 | 7.4 |
| mCCL27 | 8.5 |
| hCXCL12β | 10.3 |

Fig. 6

```
CMLV  CrmB   MKSVLYSVILFLSCIIINGRDVTPYAPSNGRCKDNEYKRHBLCCLSCPPGTYASRLCDSK
VaVBSH CrmB  MKSVLYLYILFLSC-IINGRDAAPYTPFNGKCKDYEYKRHBLCCLSCPPGTYASRLCDSK

CMLV  CrmB   TNTQCTPCGSGTFTSRNNHLPACLSCNGRCDSNQVETRSCNTTHNRICECSPGYYCILKG    CRD(1-4)
VaVBSH CrmB  TNTQCTPCGSGTFTSRNNHLPACLSCNGRCHSNQVETRSCNTTHNRICECSPGYYCLLKG

CMLV  CrmB   SSGCKACVSQTKCGIGYGVSGHTSAGDVICSPCGLGTYSRTVSSADKCEPVPSNTFNYID
VaVBSH CrmB  SSGCKACVSQTKCGIGYGVSGHTSVGDVICSPCGPGTYSHTVSSADKCEPVPHNTFNYID

CMLV  CrmB   VEINLYPVNDTSCTRTTTTGLSESISTSELTITHNHBDCDPVFREEYFSVLNKVATSGPF
VaVBSH CrmB  VEITLYPVNDTSCTRTTTTNLSESILTSELTITHNHTDCNFVFREEYFSVLNKVATSGFF

CMLV  CrmB   TGENRYQNISKVCTLNFEIKCNNKGSSSKQLTKAKNDDGIMPHSETVTLVGDCLSSVDIY    CTD
VaVBSH CrmB  TGENRYQNISKVCTLNFEIKCNNKGSSFKQLTEAKNDDGMSRSETVLAGDCLSSVDIY

CMLV  CrmB   ILYSNTNFQDYETDFTSYNAGNVLDVDSHMPGSCDIHXLITHSKPTNFL
VaVBSH CrmB  ILYSNTNAQDYETDTISYRVGNVLDRDSHMPGSCMIHXPITHSKPTRFL
```

Fig. 7

VaV CrmB | VaV CrmB CRD(1-4) | VaV CrmB CTD

VaV CrmB binding to human chemokines

| CHEMOKINE | $K_D$ (nM) |
|---|---|
| hCCL25 | 0.50 |
| hCCL28 | 0.39 |
| hCXCL12β | 4.26 |
| hCXCL13 | 5.95 |
| hCXCL14 | 6.29 |
| hCCL20 | 29.2 |
| hCL1 | 28.8 |

Fig. 10
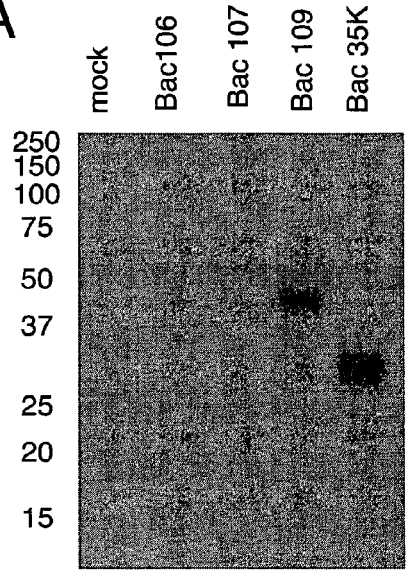 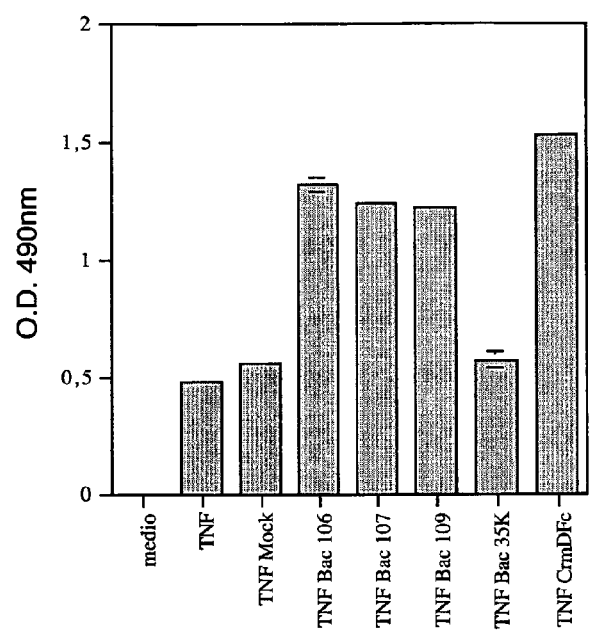

CHEMOKINE BINDING ACTIVITY OF VIRAL TNF RECEPTORS AND RELATED PROTEINS

This application is a national stage filing under 35 U.S.C. §371 of International Application No. PCT/EP2005/009449 filed on Sep. 2, 2005. This application claims priority of Spanish Patent Application No. 200402123, filed on Sep. 2, 2004.

This invention relates to the use of the C-terminal domain (CTD) of the tumour necrosis factor receptors (TNFRs) encoded by poxviruses and named cytokine response modifier B and D (CrmB and CrmD) and homologues, derivatives or fragments thereof to modulate chemokine activity and to enhance the immunomodulatory properties of TNFRs. It also relates to fusion polypeptides, pharmaceutical compositions and test kits comprising the proteins of the invention.

BACKGROUND OF THE INVENTION

Poxviruses are complex DNA viruses that encode up to 200 genes. Variola virus (VaV) was the causative agent of smallpox, one of the most devastating human diseases that was eradicated as a result of the use of vaccinia virus (VV) as a smallpox vaccine in the WHO global eradication campaign. Cowpox virus (CPV) is related to VV and is thought to be a rodent virus that causes sporadic infections in a number of mammals. Ectromelia virus (EV) is a natural mouse pathogen and the causative agent of mousepox, a generalized mouse disease with similarities to human smallpox.

The immune response has evolved as an efficient mechanism of protection from infection by pathogens such as viruses. To replicate in the immunocompetent host, viral mechanisms to evade the immune response have evolved (Alcami & Koszinowski, 2000). Poxviruses encode a broad variety of proteins that counteract the host immune response (Alcami, 2003, Seet et al., 2003). One of the immunomodulatory mechanisms encoded by poxviruses is the production of secreted proteins that bind cytokines, a family of proteins that regulate the immune response.

Four secreted TNFRs encoded by poxviruses have been described, and named Cytokine response modifier B (CrmB), CrmC, CrmD and CrmE (Hu et al., 1994, Loparev et al., 1998, Saraiva & Alcami, 2001, Smith et al., 1996). These proteins have amino acid sequence similarity to the cysteine-rich domains (CRDs) present in the human TNFRs and constituting the TNF binding extracellular domain. The viral proteins lack the transmembrane and intracellular domains of the cellular TNFRs (FIGS. 1 and 2).

All four vTNFRs have been shown to be secreted from virus-infected cells, to bind TNF and to block TNF biological activity. The CRDs of vTNFRs are predicted to bind TNF, and this has been demonstrated for the CrmB homologue encoded by myxoma virus (M-T2) (Schreiber et al., 1997), and our own experiments showing that the three N-terminal CRDs of CrmD encode TNF binding and inhibitory activity (see below).

Representative members of two of the vTNFRs named CrmB and CrmD are: CPV CrmB (SEQ ID NO 11 and 12), VaV CrmB (SEQ ID NO 9 and 10), CPV CrmD (SEQ ID No 1 and 2) and EV CrmD (SEQ ID NO 3 and 4). CrmB and CrmD have an additional CTD with no amino acid sequence similarity to cellular proteins in the databases (FIGS. 1 and 2). This domain is not required for TNF binding and its function has not been defined. Three open reading frames (ORFs) encoded by poxviruses have amino acid sequence similarity to the CTD of vTNFRs. Representative members of these ORFs are EV E12 (CTD1) (SEQ ID NO 5 and 6), EV E184 (CTD2) (SEQ ID NO 19 and 20), and CPV B21R/V218 (CTD3) (Accession No. O72758 and SEQ ID NO 13 and 14) (FIGS. 1 and 2).

A number of secreted proteins that bind chemokines have been described in several poxviruses and herpesviruses (Alcami et al., 1998, Bryant et al., 2003, Graham et al., 1997, Lalani et al., 1997, Parry et al., 2000, van Berkel et al., 2000) (Table 1). These virus-encoded chemokine binding proteins (vCKBPs) have no amino acid sequence similarity to the cellular seven-transmembrane-domain chemokine receptors or other cellular proteins (Alcami, 2003, Seet et al., 2003, Seet & McFadden, 2002). Structural and functional studies on the 35 kDa vCKBP encoded by CPV and M3 encoded by murine gammaherpesvirus 68 (MHV-68) have demonstrated that these viral proteins represent novel protein domains or structures that have the ability to bind chemokines (Alexander et al., 2002, Carfi et al., 1999). The ability of some of the vCKBPs to block leukocyte migration into infected tissues and viral pathogenesis has been demonstrated (Bridgeman et al., 2001, Graham et al., 1997, Johnston & McFadden, 2004, Lalani et al., 1999, Reading et al., 2003).

The C-terminal domain (CTD) of the viral TNF receptors (vTNFRs) cytokine response modifier B (CrmB) and CrmD have no ascribed function to date and no sequence similarity to host proteins. We found that this domain confers these vTNFRs the ability to bind several chemokines, and that the CTD expressed independently of the TNF binding domain of vTNFRs binds chemokines. This protein domain is also found in three additional poxvirus-encoded proteins predicted to be secreted, and we show that two of them encoded by the E12 gene of ectromelia virus (EV) and B21R gene of cowpox virus (CPV) bind chemokines. We propose that the CTD of vTNFRs defines a novel structural domain that binds chemokines. These proteins may modulate chemokine activity in vivo and be used to modulate adverse immune and inflammatory responses in a number of human disease conditions. The expression of this CTD fused to soluble TNFRs may enhance the immunomodulatory properties of TNFRs already used in the clinic. In addition, the CTD enhance the TNF binding activity of the N-terminal cysteine-rich domains of vTNFRs, and vTNFRs bind other members of the TNF ligand superfamily.

SUMMARY AND DESCRIPTION OF THE INVENTION

A first aspect of the present invention, comprises a C-terminal domain (CTD) of viral TNF receptors CrmB and/or CrmD from poxvirus and their homologues CTD1, CTD2 and CTD3 from poxvirus, including functional homologues, derivatives, and fragments, for use in binding chemokines and their analogues and/or to enhance the immunomodulatory properties of TNFRs.

A preferred aspect of the invention comprises CTD from CrmB and/or CrmD from poxvirus and their functional homologues CTD1, CTD2 and CTD3 from poxvirus, including homologues, derivatives, and fragments, for use in blocking binding of chemokines to corresponding cell surface receptors and/or to modulate chemokine binding activity.

Homologues of the CTD from CrmB and/or CrmD from poxvirus can be obtained, e.g. by mutation of the nucleotide sequences encoding the CDT from CrmB and/or CrmD and expression from the mutated sequence, and/or by use or derivation from related gene sequences. Alternatively, they can be obtained, e.g. by identifying gene sequences homologous to the CTD from CrmB and/or CrmD by screening databases containing either protein sequences or nucleotide sequences encoding proteins, for example by screening the Swissprot database in which homology can be determined using the Blast program, e.g. using any of the possible algorithms. An acceptable level of homology over the whole sequence is at least about 20%, e.g. about 30%. Homology of a functional fragment of the CTD from CrmB and/or CrmD with other proteins can be lower than this, e.g. about 10%.

Functional homologues, including derivatives or fragments of the CTD from CrmB or CrmD or the CTD homologues (CTD1, CTD2 and CTD3) can be checked for their capacity to bind chemokines by appropriate methods equivalent to the cross-linking assays using for example radiolabelled chemokines or with other methods measuring protein-protein interactions such as Surface Plasmon Resonance (SPR, BIAcore).

In a more preferred embodiment of the invention, the CTD from CrmB comprises any of SEQ ID NO 26 or SEQ ID NO 28; the CTD from CrmD comprises any of SEQ ID NO 22 or SEQ ID NO 24; and the CTD homologues (CTD1, CTD2 and CTD3) comprises any of the following: SEQ ID NO 8, SEQ ID NO 14, SEQ ID NO 6, SEQ ID NO 20, SEQ ID NO 18, SEQ ID NO 16 and the proteins encoded by genes CPV V201 (Accession No. Q8QMP4), D12L (Accession No. P87598), B6R (Accession No. O72743) or B21R (Accession No. O72758).

A second aspect of the invention provides a nucleic acid molecule which encodes for the CTD of the invention including homologues derivatives, and fragments. It also falls within the invention the complementary strand of the latter nucleic acids; and a nucleic acid molecule which differs from the sequence coding for a CDT according to the invention including homologues, derivatives and fragments due to the degeneracy of the genetic code.

In a preferred embodiment of the invention, the sequences coding for the CTD from CrmB comprises any of SEQ ID NO 25 or 27; the sequences coding for the CTD from CrmD comprises any of SEQ ID NO 21 or SEQ ID NO 23; and the sequences coding for the CTD of the functional homologues comprises any of the sequences encoded by the following genes: V014 (SEQ ID NO 7), V201, V218 (SEQ ID NO 13), D12L, B6R, B21R, E12 (SEQ ID NO 5), E184 (SEQ ID NO 19), VACWR189 (SEQ ID NO 17) or VACWR206 (SEQ ID NO 15) (FIGS. 1 and 2).

According to a third aspect of the invention, a fusion polypeptide can be made comprising any of the CTD from CrmB or CrmD or CTD homologues (CTD1, CTD2 and CTD3), including functional homologues, derivatives and fragments fused to a polypeptide sequence of the same or other origin.

In a preferred embodiment of the invention, the CTD from CrmB or CrmD or CTD homologues (CTD1, CTD2 and CTD3) including functional homologues, derivatives and fragments can be coupled with other substances, either covalently or non-covalently. Coupling products can be fusion proteins. The expression of CTD fused to soluble TNFRs enhances the immunomodulatory properties of TNFRs already use in clinic. The C-terminal domain provides a molecular scaffolding that enhances the TNF binding activity of the N-terminal CRD; e.g. CRD (1, 2) binding properties are enhance in this way. In addition this enhancement can make vTNFRs bind other members of the TNF ligand superfamily.

Thus in a further aspect of the invention, the fusion polypeptide comprises the CTD from CrmB or CrmD or their CTD homologues (CTD1, CTD2 and CTD3), including functional homologues, derivatives and fragments fused to the N-terminal TNF binding domain of vTNFRs, preferably fused to TNFRs of human origin.

In a still further embodiment of the invention, the fusion proteins made comprising any of the CTD from CrmB or CrmD or CTD homologues (CTD1, CTD2 and CTD3), including functional homologues, derivatives and fragments fused to a polypeptide sequence of other origin confers chemokine binding properties to the latter.

For certain purposes, coupling partners can be coupled to the CTD from CrmB or CrmD or their CTD homologues (CTD1, CTD2 and CTD3), including functional homologues, derivatives and fragments by known chemical coupling methods, for example biotinylation of one partner and derivatisation of the other with a binding partner of biotin, such as avidin.

Any of the CTD from CrmB or CrmD or their CTD homologues (CTD1, CTD2 and CTD3), including functional homologues, derivatives and fragments as described above (Proteins of the Invention), can for example be used to bind either chemokines and their analogues with an animal species origin or specificity corresponding to the host range of the parent virus from which the protein comes, and/or chemokines and their analogues with human origin and/or specificity.

Amongst derivatives of the Proteins of the Invention which are within the scope of the invention are polypeptides having sequences encoding for proteins of the invention modified by deletion or substitution, which retain the chemokine binding properties of the protein of the invention. For example, it can be useful to delete any immunogenic amino acid motifs, or replace such motifs with a less immunogenic amino acid sequence. Alternatively, a modification which can induce immunological tolerance in a host can be introduced into the sequences that code for the Proteins of the Invention.

The invention also extends to nucleotide sequences e.g. DNA cassettes incorporating suitable promoters encoding the proteins of the invention and its modified forms including homologues, such as fragments or their fusion products with other polypeptides, and such expression cassettes included in suitable plasmid or other vectors, e.g. viral vectors.

The Proteins of the Invention can for example be used to bind C chemokines, CC chemokines, CXC chemokines or CX3C chemokines. In accordance with an aspect of the invention, the Proteins of the Invention can be used to block the binding of such chemokines to their receptors or to inhibit the biological activity, whether in-vitro, e.g. in biological samples or in-vivo.

This effect can be exploited for example in specific binding tests using labelled reactants, e.g. for diagnostic and measurement purposes. The labelled reactant can be either of the Proteins of the Invention, or a chemokine, or a chemokine receptor, according to the configuration of the test for desired purposes in hand.

Accordingly, an aspect of the invention also lies in compositions for carrying out such tests, e.g. the labelling product of the proteins of the invention; calibrated test aliquots of either of these: the product of binding the proteins of the invention to a solid phase suitable to take part in a specific binding test as mentioned herein; calibrated test aliquots of one of the binding partners in the reaction; and test kits associating two or more of such reagents. The test can be for example an assay for a chemokine or for a chemokine receptor.

The binding effect can also be exploited in the inhibition of effects mediated by chemokines that can be bound by the Proteins of the Invention.

According to a further aspect of the invention a pharmaceutical composition comprising a CTD from CrmB and/or CrmD and/or the CTD homologues (CTD1, CTD2 and CTD3), and/or functional homologue, derivative or fragment thereof and/or fusion with other proteins and/or expression cassettes and/or plasmids or other vectors, can be used in binding to a chemokine or a chemokine analogue in vivo, or in blocking binding of a chemokine to a corresponding cell surface receptor in vivo, to produce an immunomodulatory effect.

According to a still further aspect of the invention a pharmaceutical composition can comprise a protein of the invention, for use as an anti-inflammatory agent, in appropriate therapeutic (anti-inflammatory) amount.

The proteins of the invention can be formulated with compatible per se conventional pharmaceutical excipients for delivery to a subject to be treated.

According to a preferred embodiment of the invention, a nucleotide sequence encoding any of the proteins of the invention or fusion proteins comprising the Proteins of the Invention can be inserted under control of a suitable promoter. The gene delivery system can be a viral or non viral vector system. Such a vector can be used to confer on a target transfected cell the ability to produce the proteins of the invention for example for anti-inflammatory purposes when the target cell is in-vivo in a host that is the subject of treatment. Such anti-inflammatory purposes can include for example use to inhibit effects mediated by chemokines, e.g. by chemokines which promote or are associated with disease, for example an inflammatory disease such as rheumatoid arthritis. Anti-inflammatory purposes also include reduction of host immune response against elements of the vector delivery system and/or against other gene products expressed in the target cell after gene delivery by a vector system, whether it is from the same vector as that which delivers the proteins of the invention or from a separate delivery vector for such another delivered gene.

The proteins of the inventions or vectors expressing the Proteins of the Invention can be administered to cells in vivo, for example by any suitable systemic delivery route. Alternatively the administration can be targeted, e.g. by direct injection, such as by intravenous injection at or near the site of the target cells and/or site of inflammation in the subject to be treated.

Forms of administration can be chosen to limit the immune response of the host to the proteins of the invention. For example, the proteins of the invention or a vector system expressing them can be delivered with another immunosuppressant or anti-inflammatory substance.

A still further aspect of the invention relates to VV vaccines against free of the proteins of the invention and/or vTNFRs. Some vTNFRs and CTD-related proteins are expressed by some VV strains used as smallpox vaccine in humans or as recombinant viral vectors for expression of proteins from other pathogens to induce immunity. Neutralization of the chemokine binding activities of these proteins may decrease adverse effects reported after smallpox vaccination with UV, by limiting viral replication and/or virus-induced immunopathology. Antibodies or reagents that neutralize the chemokine binding activity of the vTNFRs or CTDs can attenuate human smallpox, protect from fatal human smallpox and reduce the adverse effects caused by VV vaccination.

Another aspect of the invention includes a method of detection of a chemokine or chemokine analogue by incubating a sample that contains a chemokine or chemokine analogue with a reagent comprising the Proteins of the Invention.

Another aspect of the invention refers to the use of the Proteins of the Invention to produce a medicament to treat the adverse effects caused by VV vaccination or the pathology caused by smallpox, based on antibodies to the Proteins of the Invention or reagents that inhibit the chemokine binding activity of vTNFRs or the CTD homologues.

Other aspects of the present invention will result obvious to a person of ordinary skill in the art.

BRIEF DESCRIPTION OF THE FIGURES

FIG. 1. Schematic representation of vTNFRs and CTD homologues in different viruses. The gene name in each virus is indicated.

FIG. 2. Multiple sequence alignment of vTNFRs CrmB and CrmD with CTD homologues. (Alignment 1: SEQ ID NOS 2, 4, 10, 12, 6, 8, 18, 20, 14 & 16 respectively; Alignment 2: SEQ ID NOS 10, 12, 2 & 4 respectively; Alignment 3: SEQ ID NOS 6, 8, 18, 20, 14 & 16 respectively.)

FIG. 3. Identification of EV CrmD as an IL-8 (CXCL8) binding protein. (a) Cross-linking of 125I-IL-8 to media from EV-infected cells showed the presence of an IL-8 binding activity not expressed by VV. (b) EV full-length CrmD expressed from a recombinant VV binds IL-8 whereas CrmD CRD(1-4) does not. (c) Binding of 125I-IL-8 to recombinant CrmD was not inhibited in the presence of excess human or mouse TNF. (d) Cross-linking of 125I-IL-8 to CPV CrmD and CrmB expressed in the baculovirus system.

FIG. 4. Role of the CrmD CRD and CTD in TNF binding and activity inhibition. (a) Schematic representation of the constructs containing combinations of the EV CrmD CRDs and CTD. (b) Competition of binding of 125I-TNF to U937 cells by supernatants from cells infected with VV recombinants expressing the indicated CrmD constructs. (c) Biological activity of recombinant CrmD constructs determined as the percentage of TNF-induced cytotoxicity in mouse L929 cells in the presence of increasing doses of supernatants of cells infected with the indicated recombinant VVs or VV WR. (d) Inhibition of TNF-induced cytotoxicity by supernatants from cells infected with the indicated recombinant baculoviruses.

FIG. 5. Chemokine binding to EV CrmD. Purified recombinant EV CrmD protein was amine-coupled to a CM5 biosensor chip to a level of 5000 RU. This chip was used to screen the binding to all commercially available human chemokines in a BIAcoreX (Uppsala, Sweden). In all cases, 30 µl of a 100 nM chemokine solution was injected at 10 µl/min flow. Maximum binding level was plotted against the binding level after 120 s of dissociation (stability of complex) for each chemokine. Inset: Affinity constants for the shown chemokines as determined by SPR kinetic analyses. For kinetic analyses, purified recombinant EV CrmD protein was amine-coupled to a CM5 biosensor chip to a level of 1200 RU (Rmax<200 RU). Different chemokine concentrations were injected at a flow rate of 30 µl/min for 2 min and dissociation monitored for an additional 5 min. Fitting of the curves was performed with the BIAevaluation software using a 1:1 Langmuir binding model.

FIG. 6. Alignment of the amino acid sequence of camelpox virus (CMLV) and VaV CrmB proteins. Conserved residues are indicated with an asterisk. Positions mutated are shown in red. The CRD (1-4) and CTD are indicated. (SEQ ID NOS 42 & 10 are disclosed respectively in order of appearance).

FIG. 7. Different domains of VaV CrmB bind to TNF and chemokines. Binding of human TNFα (red) and human CXCL12β (CK, blue) to full-length VaV CrmB, VaV CrmB CRD (1-4) or VaV CrmB CTD purified proteins analyzed by SPR.

FIG. 8. Inhibition of TNF and chemokine biological activity by VaV CrmB. (a) Inhibition of TNF-induced cytotoxicity. TNF was preincubated for 2 h at 37 C with the indicated amount of purified recombinant proteins in ⁻¡□¡ of complete DMEM supplemented with actinomycin D (4 μg/ml). The mixture was then added to $2\times10^4$ L929 cells seeded the day before in 96-well plates and cell death assessed 16 to 18 h later. O.D. 490 nm of cuadruplicates (mean±SD) is plotted each case. "Celulas"/"cel ActD": controls for cell viability; "TNF": control for cell death; "CrmB": TNF preincubated with VaV CrmB; "CRD": TNF preincubated with VaV CrmB CRD(1-4); "IgG1": TNF preincubated with IgG1, control for specificity. (b) Chemotaxis assay. Human CCL25 (100 nM) alone or in the presence of increasing amounts of purified recombinant protein was incubated at 37 C for 30 minutes and placed in the lower compartment of a 24 well-Transwell chamber. After this period, $5\times10^5$ MOLT-4 cells were added in 100 □l complete RPMI containing 0.1% FCS to the top well and the plate incubated in a 37° C. for 4 hours. % of migration of MOLT-4 cells towards the bottom well was determined by FACS analysis. 100% migration was set as the number of cells that migrate in the presence of chemokine only.

FIG. 9. Chemokine binding to VaV CrmB. Purified recombinant VaV CrmB protein was amine-coupled to a CM5 biosensor chip to a level of 5000 RU. This chip was used to screen the binding to all commercially available human chemokines in a BIAcoreX (Uppsala, Sweden). In all cases, 30 μl of a 100 nM chemokine solution was injected at 10 μl/min flow. Maximum binding level was plotted against the binding level after 120 s of dissociation (stability of complex) for each chemokine. Inset: Affinity constants for the shown chemokines as determined by SPR kinetic analyses. For kinetic analyses, purified recombinant VaV CrmB protein was amine-coupled to a CM5 biosensor chip to a level of 1200 RU (Rmax<200 RU). Different chemokine concentrations were injected at a flow rate of 30 μl/min for 2 min and dissociation monitored for an additional 5 min. Fitting of the curves was performed with the BIAevaluation software using a 1:1 Langmuir binding model.

FIG. 10. Fusion of the VV 35 kDa vCKBP to CRD(1-4) of VaV CrmB confers CrmB the ability to bind chemokines. (a) Cross-linking assay for chemokine binding. Supernatants from High5 cells mock-infected of infected with the recombinant baculoviruses "Bac VaV CrmB CRD(1-4)" (Bac106), "Bac VaV CrmB" (Bac107), and "Bac VaV CrmB CRD(1-4)/35K" (Bac109) were incubated with 400 μM of $^{125}$I-CCL3. Complexes between the recombinant proteins and CCL3 were cross-linked by using EDC and products analysed by SDS-PAGE and autoradiography. (b) Inhibition of TNF-induced cytotoxicity. TNF was preincubated for 2 h at 37 C with the corresponding supernatants in ¯¡□¡ of complete DMEM supplemented with actinomycin D (4 μg/ml). The mixture was then added to $2\times10^4$ L929 cells seeded the day before in 96-well plates and cell death assessed 16 to 18 h later. O.D. 490 nm is plotted against the different samples.

DETAILED DESCRIPTION OF THE INVENTION

The invention, and materials and methods applicable to carrying out embodiments thereof, are further illustrated in the following examples, but without intent to limit its scope.

EXAMPLES

Example 1

Materials and Methods 1.1.—Poxviruses

CPV, EV and VV were propagated in vitro by infecting confluent monolayers of Bsc-I cells.

1.2.—Cloning of Camelpox CrmB and Generation of VaV CrmB

ORF 264 of strain CMS of camelpox virus, corresponding to the CrmB gene was amplified by PCR using oligonucleotides CMLV 264 Eco (5'-GCGGAATTCATGAAGTCCG-TATTATACTCG) (SEQ ID NO: 29) and CMLV 264 Xho (51-GCGCTCGAGTAAAAAGTGGGTGGGTTTGG) (SEQ ID NO: 30) and purified CMLV DNA as a template. The PCR product was cloned into EcoRI/XhoI digested pBacl (Novagen) to generate plasmid pRA1. The absence of mutations in the amplified gene was confirmed by DNA sequencing. The DNA corresponding to the VaV (strain Bangladesh 1975; ORF 188) was obtained by multiple-site directed mutagenesis of plasmid pRA1 using the "QuikChange Multi Site-Directed Mutagenesis Kit (Stratagene)" following the manufacturer's instructions. The mutations introduced are shown in FIG. 6. After several consecutive rounds of site-directed mutagenesis, plasmid pRA105 was obtained. This plasmid contains the sequence coding for VaV (BSH 1975 strain) CrmB fused to a C-terminal His tag provided by the original pBad plasmid. The presence of all the mutations and absence of unwanted additional mutations was confirmed by direct sequencing.

1.3.—Construction of Recombinant Baculoviruses and Vaccinia Viruses Expressing CrmD from EV or CPV For expression in the baculovirus system, DNA encoding full length or truncated versions of CrmD (Table 3) was PCR-amplified with the specific oligonucleotides (Table 4), and cloned into pBAC-1. Recombinant baculoviruses were generated by homologous recombination in SF21 insect cells transfected with recombinant pBAC-1 plasmids and the linearized baculovirus DNA as described (Alcami et al., 1998).

vTNFRs were also expressed from a VV expression system. The genes of interest were cloned into pMJ601 for expression of the gene from a strong VV promoter (Davison & Moss, 1990). The gene of interest is inserted into the thymidine kinase locus of the VV genome by homologous recombination, and the recombinant VV selected in the presence of bromodeoxiuridine and identified by colour selection (expression of □-galactosidase and staining with X-gal). VTNFRs were expressed from VV Western Reserve, a virus strain that does not encode TNF binding activity (Alcami et al., 1999).

1.4.—Generation of Recombinant Baculoviruses Expressing VaV CrmB, VaV CrmB CRD(1-4), VaV CrmB CTD, EV E12, EV E184, CPV V218 and VaV CrmB CRD(1-4) Fused to CPV 35 kDa Protein The full length VaV CrmB gene fused to a C-terminal His tag was subcloned into EcoRI/SphI digested pFastBad (Invitrogen) to generate pRA107. The N-terminal domain of VaV CrmB including the four CRDs and corresponding to residues 1 (M) to 192 (C) was amplified by PCR using oligonucleotides VaV 188 Eco (5'-GCGGAATTCATGAAGTCCGTAT-TATACTTG) (SEC) ID NO: 31) and VaV 188 CRDsI-4 Xho (5'-GCGCTCGAGACACGATGTGTCGTTAACTGG) (SEQ ID NO: 32) using pRA107 as a template. The amplified fragment was cloned in-frame with a C-terminal his tag provided by the EcoRI/XhoI digested pBad (Novagen) to generate pRA99. pRA99 was digested with EcoRI/SphI and the fragment carrying the VaV CrmB CRDs 1 to 4 fused to the His tag cloned into pFastBad as before to generate pRA106. The CTD of VaV CrmB (residues T194 to L348) was PVR amplified with oligonucleotides VaV 188 Cter-PfIMI (5'-CGC-CCACCCAATGGAACTAGGACGACCAC-TACCGG) (SEQ ID NO: 33) and H347R 3 using pRA107 as a template. This fragment was digested with PfmII and XhoI and cloned into pRA107 digested with the same enzymes. This generates pRA108, a plasmid that encodes a fusion protein composed of the 29 N-terminal residues of VaV CrmB (which includes the predicted signal peptide) followed by the CTD of CrmB and an additional His tag. The absence of unwanted mutations in pRA106, pRA107 and pRA108 was confirmed by sequencing the complete inserts in all cases.

The EV gene E12 was amplified by PCR using oligonucleotides E1 (5'-GCGGGA-TCCATGATAAACATAAACAT-AAACACAATAC) (SEQ ID NO: 34) and E2 (5'-GCGGCG-GCCGCAT-TAATAGTTCTAGTAGCGCAAG) (SEQ ID NO: 35) and purified EV (strain naval. Cam) DNA as a template. The PCR product was cloned into Bam HI/Not I digested pBad (Novagen) generating plasmid pMS51. The E12 gene was subcloned into Bam HI/Xho I-digested pRA106 to give plasmid pAH18, which contains the E12 gene fused to a C-terminal sequence coding for a His-tag in a pFastbac (Invitrogen) backbone. The CPV Brighton Red strain ORF V218 was PCR-amplified using oligonucleotides 5V218 EcoRI (5'-CGCGAATTCATGATGATATACGGAT-TAATAGC) (SEQ ID NO: 36) and 3V218 Sail (5'-GCGGTC-GACACCATCGACACCACTCATC) (SEQ ID NO: 37) and purified viral DNA as a template. The PCR product was cloned into Eco RI/Xho I digested pRA106 to generate plasmid pAH17. which contains the CPV V218 gene fused to a C-terminal sequence coding for a His-tag in a pFastbac (Invitrogen) backbone. The fragment corresponding to residues S23 to V246 of the CPV (strain Brighton Red) 35 kDa protein was PCR-amplified using oligonucleotides 5'35 KBR-S23 (5'-CGCCTCGAGTCATTCTCATCCTCATCCTC) (SEQ ID NO: 38) and 3' 35 KBR (-stop)(5'-CGCCTCGAGGACA-CACGCTATAAGTTTTGC) (SEQ ID NO: 39) and purified viral DNA as a template. The PCR product was cloned into Xho I digested pRA106 to generate plasmid pRA109. This plasmid carries the sequence encoding VaV CrmB CRD (1-4) fused in frame to the sequence encoding CPV 35 kDa vCKBP without its signal peptide and with a C-terminal His tag in a pFastBac backbone (Invitrogen).

Recombinant baculoviruses were obtained using the Bac-to-Bac expression system (Invitrogen) as described by the manufacturer. Briefly the plasmids pRA106, pRA107, pRA108, pRA109, pAH17 and pAH18 were transformed into competent DH10Bac bacteria, were a transposition event generates the corresponding recombinant bacmids. These were purified and transfected into High5 insect cells and three days after transfection, the recombinant baculoviruses vBac106, vBac107, vBac108, vBac109, vBacAH17 and vBacAH18 harvested from the cell culture supernatants. These viruses were further amplified in one single step to generate a high titer recombinant virus stock for protein production.

The E184 gene from EV was PCR-amplified with the oligonucleotides 5'E184 (5'-GCGGAATTCATG-TATAAAAAACTAATAACGTTT) (SEQ ID NO: 40) and 3'E184 XhoI (51-CGCCTCGAGAAAAT-CATATTTTGAATAATATGTA) (SEQ ID NO: 41) and purified EV DNA as template. The PCR product was cloned into the pRA106 plasmid digested with EcoRI and XhoI, generating pAH11. The correct DNA sequence was confirmed. Plasmid pAH11 was used to generate the recombinant baculovirus vBacAHH, as described above, expressing the EV E184 protein fused to a histidine tag to facilitate the purification of the protein.

1.5.—Protein Expression and Purification

To express the recombinant proteins, High5 cells were infected at high multiplicity (10 pfu/cell) and the supernantants from infected cultures harvested at three days post infection (d.p.i.). The presence of proteins in these supernatants was confirmed by Western blot and/or, in the case of the full length and N-terminal VaV CrmB constructs, a TNF binding assay in solution (Alcami et al., 1999). The samples were concentrated to approximately 2.5 ml on a stirred ultrafiltration cell (Amicon) using YM-3 membranes (Millipore) and buffer exchanged into binding buffer (50 mM phosphate, 300 mM NaCl, 10 mM Imidazole, pH 7.4) on PD-10 desalting columns (Amersham-Pharamcia Biosciences). The His-tagged recombinant proteins were affinity-purified using Vivapure Metal Chelate columns (Vivascience) following the manufacturer's recommendations. The purity and amount of purified proteins was checked on Coomassie-blue stained SDS-polyacrylamide gels. For TNF protection and chemotaxis inhibition assays, recombinant proteins were dialyzed against PBS.

1.6.—Biomolecular Interaction Analysis by Surface Plasmon Resonance (SPR)

Cytokine binding specificity and affinity constants were determined using a BIAcore X biosensor (Biacore, Uppsala, Sweden). For ligand screening experiments, purified recombinant proteins were amine-coupled to CM5 chips to a level of approx. 5000 RU (5000 pg/mm$^2$) in each case. Commercially available cytokines (Peprotech, R&D Systems) were then injected at 100 nM in HBS-EP buffer (10 mM Hepes, 150 mM NaCl, 3 mM EDTA, 0.005% (v/v) surfactant P20; pH 7.4) at a flow rate of 5 μl/min and association and dissociation monitored. The surface was regenerated after each injection using 10 mM glycine-HCl pH2.0. For kinetic analysis, the recombinant proteins were immobilised at low densities (Rmax<200 RU). Different concentrations of the corresponding analyte were then injected at a flow rate of 30 μl/min over a 2 min period and allowed to dissociate for an additional 5 min. All Biacore sensorgrams were analysed using BIAevaluation 3.2 software. Bulk refractive index changes were removed by subtracting the reference flow cell responses and the average response of a blank injection was subtracted from all analyte sensorgrams to remove systematic artifacts. Kinetic data were globally fitted to a 1:1 Langmuir model.

1.7.—Inhibition of TNF-Induced Cytotoxicity

TNF-induced cytotoxicity assays were performed on mouse L929 cells as described previously (Loparev et al., 1998, Saraiva & Alcami, 2001, Schreiber et al., 1997, Smith et al., 1996). TNF (20 ng/ml) (R&D Systems) was preincubated for 2 h at 37 C with purified recombinant proteins in ı□l of complete DMEM supplemented with actinomycin D (4 μg/ml) (Sigma). The mixture was then added to $2\times10^4$ cells seeded the day before in 96-well plates and cell death assessed 16 to 18 h later using the "CellTiter 96® Aqueous One Solution cell proliferation assay" (Promega) following the manufacturer's recommendations.

1.8.—Chemotaxis Assay

The migration of MOLT-4 cells was assessed using 24 well Transwell® plates with 3 μm pore size filters (Costar) as described previously (Zaballos et al., 1999). Briefly, human CCL25 (100 nM) (R&D Systems) alone or in the presence of increasing amounts of purified recombinant protein was incubated at 37 C for 30 minutes and placed in the lower compartment. After this period, 5×10⁵ MOLT-4 cells were added in 100 μl complete RPMI containing 0.1% FCS to the top well and the plate incubated in a 37° C., 5% $CO_2$, 95% humidified incubator. Migration of MOLT-4 cells towards the bottom well was determined after 4 hours by flow cytometry.

Example 2

Results 2.1.—The vTNFR CrmD Encoded by EV and CPV Binds Chemokines

Searching for novel viral secreted proteins that bind chemokines, we performed cross-linking assays with 125I-CXCL8 and identified a novel secreted vCKBP encoded by the poxvirus EV (FIG. 3a). This activity was absent in VV samples and of higher molecular size than the 35 kDa vCKBP encoded by VV and other poxviruses, a protein that can cross-link CXCL8 but does not block its biological activity due to its low affinity for CXCL8 (Alcami et al., 1998, Graham et al., 1997, Lalani et al., 1998). Unexpectedly, we found that the vTNFR CrmD encoded by EV, known to bind TNF, has the additional property of binding CXCL8 (FIG. 3b). Using truncated versions of the CrmD protein expressed in the VV expression system, we have shown that the 3 N-terminal CRDs of CrmD are necessary to block TNF activity (FIGS. 4a,b,c) and the CTD is not necessary for TNF binding but confers CrmD the ability to bind chemokines (FIG. 3b). Different domains of CrmD appear to be involved in TNF and chemokine binding since cross-linking of CXCL8 to CrmD cannot be blocked in the presence of TNF (FIG. 3c) and binding of TNF to CrmD is not inhibited in the presence of CXCL8 (not shown). Using the Surface Plasmon Resonance (SPR, BIAcore X) technology we have tested the potential interaction of purified EV CrmD to all commercially available chemokines of human and mouse origin, and have identified that CrmD binds with high affinity several chemokines (FIG. 5).

2.2.—The vTNFR CrmB Encoded by CPV and VaV Binds Chemokines

To test whether the other vTNFR encoding an extended CTD binds chemokines, we expressed CrmB from CPV in the baculovirus system and showed that it binds CXCL8 in cross-linking assays (FIG. 3d). CrmB is also encoded by the human pathogen VaV, the causative agent of smallpox. We have generated the CrmB gene of VaV by extensive site-directed mutagenesis of the CrmB gene from the related camelpox virus (FIG. 6) and expressed the protein in the baculovirus system. We first tested that purified VaV CrmB protein binds TNF (FIG. 7) and inhibits TNF biological activity (FIG. 8a). CrmB was also tested for binding to all available human chemokines by SPR and we demonstrated that CrmB binds with high affinity a number of chemokines (FIG. 9). A truncated version of VaV CrmB lacking the CTD did not bind chemokines (FIG. 7). Moreover, expression and purification of the CTD of VaV CrmB has demonstrated that the CTD encodes the chemokine binding activity of CrmB (FIG. 7). This is corroborated by SPA analysis showing that TNF and chemokines bind to different sites in CrmB (not shown).

2.3.—The vTNFR CrmB Encoded by VaV Blocks Migration of Molt4 Cells Induced by CCL25 In Vitro The high affinity of the vTNFRs CrmB and CrmD for some chemokines suggests that these viral proteins may act as decoy receptors sequestering chemokines and preventing chemokines from binding to their specific receptors on leukocytes and inducing signals that trigger cell migration. We show that VaV CrmB inhibits the migration of Molt4 cell, expressing relevant receptors, in response to the chemokine CCL25 (FIG. 8b).

2.4.—Proteins Related to the CTD of vTNFRs (CTD Homologues) Bind Chemokines

As indicated above, three proteins encoded by poxviruses have amino acid sequence similarity to the CTD of the vTNFRs (CrmB and CrmD) (FIGS. 1 and 2). These proteins, named CTD1, CTD2 and CTD3 have an N-terminal signal peptide suggesting that they are secreted. Expression of two of these proteins, EV E12 (CTD1), EV184 (CTD2) and CPV B21R (CTD3), in the baculovirus system has shown that both proteins are secreted into the medium. Purified EV E12 protein was tested for binding to all mouse chemokines and found to bind several chemokines with high affinity (Table 2). In addition, we have determined by SPR that the purified proteins CPV B21R and V E184 bind CCL21, CCL24, CCL25, CCL27, CCL28, CXCL10, CXCL11, CXCL12β, CXCL13 and CXCL14 from mouse, and human CCL26 The VV WR B7R (CTD2) has been shown to be translocated to the lumen of the endoplasmic reticulum and to be retained inside the cell rather than being secreted (Price et al., 2000). Some of the CTD homologues may function to block the activity of chemokines such as CCL27 that have been known to be expressed inside the cell as well (Gortz et al., 2002). A VV mutant lacking the B7R gene is attenuated in a murine intradermal model (Price et al., 2000).

2.5.—The vTNFRs CrmD from EV and CrmB from VaV Bind Other TNF Ligand Superfamily Members TNF is a member of a large family of immune mediators with structural similarities, known as the TNF ligand (TNFL) superfamily (Locksley et al., 2001, Wallach, 2001). EV CrmD and VaV CrmB were tested by SPR for binding to all commercially available TNF ligand superfamily members and found to bind APRIL (TNFL13) (CrmD Kd 110 μM; CrmB Kd 2 nM) and LIGHT (TNFL14) (CrmD Kd 140 nM; CrmB Kd 2 nM). This suggests that CrmD and CrmB (and maybe other vTNFRs) may inhibit the biological activity of several TNF ligand superfamily members.

2.6.—The CTD of vTNFRs May Influence the Ability of the CRDs to Bind TNF with High Affinity As shown above, a truncated vTNFR CrmD comprising the N-terminal CRD(1,2) looses affinity for TNF and does not block TNF biological activity, while CRD(1-3) binds TNF and inhibits its activity (FIGS. 4a,b,c). Surprisingly, when CRD(1,2) is expressed fused to CTD it recovers TNF inhibitory activity, showing that CTD may enhance the TNF binding activity of the N-terminal CRDs of the vTNFR (FIG. 4d).

2.7.—Virus-Encoded Proteins are Formed of Domains that Bind Immune Ligands independently The data shown here indicate that the vTNFRs CrmB and CrmD are composed of two independent domains (FIGS. 1 and 2). The N-terminal CRDs have the ability to bind TNF while the CTD binds chemokines in an independent fashion. This is demonstrated by the finding that CRD(1,4) from CrmB retains TNF binding activity and CTD from CrmB has chemokine binding activity when expressed independently. The concept that these regions of viral proteins represent structural modules or domains that bind immune mediators is emphasized by the finding that: (1) purified CTD of VaV CrmB binds chemokines (FIG. 7); (2) the CTD of CrmB and CrmD encoded by CPV can be exchanged and still confer chemokine binding activity (not shown); (3) three different proteins related to vTNFR CTD (EV E12, EV E184 and CPV B21R) encode chemokine binding activity (Table 2); and (4) fusion of the CPV 35 kDa vCKBP to the CRD(1,4) of VaV CrmB confers this protein the ability of binding chemokines without affecting the TNF-inhibitory activity (FIG. 10). Therefore, these viral domains may be exchanged or combined to generate immune modulatory proteins that block the activity of several cytokines. We propose that the CTD of vTNFRs defines a novel protein structure/domain that binds immune proteins such as chemokines or other proteins involved in the immune system and confers vTNFRs the ability to bind other immunomodulatory proteins in addition to TNF.

REFERENCES

Alcami, A. (2003). Viral mimicry of cytokines, chemokines and their receptors. *Nat Rev Immunol* 3, 36-50.

Alcami, A., Khanna, A., Paul, N. L. & Smith, G. L. (1999). Vaccinia virus strains Lister, USSR and Evans express soluble and cell-surface tumour necrosis factor receptors. *J. Gen. Virol.* 80, 949-59.

Alcami, A. & Koszinowski, U. H. (2000). Viral mechanisms of immune evasion. *Immunol. Today* 21, 447-55.

Alcami, A., Symons, J. A., Collins, P. D., Williams, T. J. & Smith, G. L. (1998). Blockade of chemokine activity by a soluble chemokine binding protein from vaccinia virus. *J. Immunol.* 160, 624-33.

Alexander, J. M., Nelson, C. A., van Berkel, V., Lau, E. K., Studts, J. M., Brett, T. J., Speck, S. H., Handel, T. M., Virgin, H. W. & Fremont, D. H. (2002). Structural basis of chemokine sequestration by a herpesvirus decoy receptor. *Cell* 111, 343-56.

Bridgeman, A., Stevenson, P. G., Simas, J. P. & Efstathiou, S. (2001). A secreted chemokine binding protein encoded by murine gammaherpesvirus-68 is necessary for the establishment of a normal latent load. *J Exp Med* 194, 301-12.

Bryant, N. A., Davis-Poynter, N., Vanderplasschen, A. & Alcami, A. (2003). Glycoprotein G isoforms of some alphahepesviruses function as broad-spectrum chemokine binding proteins. *EMBO J.* 22, 833-846.

Carfi, A., Smith, C. A., Smolak, P. J., McGrew, J. & Wiley, D.C. (1999). Structure of a soluble secreted chemokine inhibitor vCCI (p35) from cowpox virus. *Proc. Natl. Acad. Sci. U.S.A.* 96, 12379-83.

Davison, A. J. & Moss, B. (1990). New vaccinia virus recombination plasmids incorporating a synthetic late promoter for high level expression of foreign proteins. *Nucleic Acids Res* 18, 4285-6.

Gortz, A., Nibbs, R. J., McLean, P., Jarmin, D., Lambie, W., Baird, J. W. & Graham, G. J. (2002). The chemokine ESkine/CCL27 displays novel modes of intracrine and paracrine function. *J Immunol* 169, 1387-94.

Graham, K. A., Lalani, A. S., Macen, J. L., Ness, T. L., Barry, M., Liu, L. Y., Lucas, A., Clark-Lewis, I., Moyer, R. W. & McFadden, G. (1997). The T1/35 kDa family of poxvirus-secreted proteins bind chemokines and modulate leukocyte influx into virus-infected tissues. *Virology* 229, 12-24.

Hu, F., Smith, C. A. & Pickup, D. J. (1994). Cowpox virus contains two copies of an early gene encoding a soluble secreted form of the type II TNF receptor. *Virology* 204, 343-356.

Johnston, J. B. & McFadden, G. (2004). Technical knockout: understanding poxvirus pathogenesis by selectively deleting viral immunomodulatory genes. *Cell Microbiol* 6, 695-705.

Lalani, A. S., Graham, K., Mossman, K., Rajarathnam, K., Clark-Lewis, I., Kelvin, D. & McFadden, G. (1997). The purified myxoma virus gamma interferon receptor homolog M-T7 interacts with the heparin-binding domains of chemokines. *J Virol* 71, 4356-63.

Lalani, A. S., Masters, J., Graham, K., Liu, L., Lucas, A. & McFadden, G. (1999). Role of the myxoma virus soluble CC-chemokine inhibitor glycoprotein, M-T1, during myxoma virus pathogenesis. *Virology* 256, 233-45.

Lalani, A. S., Ness, T. L., Singh, R., Harrison, J. K., Seet, B. T., Kelvin, D. J., McFadden, G. & Moyer, R. W. (1998). Functional comparisons among members of the poxvirus T1/35 kDa family of soluble CC-chemokine inhibitor glycoproteins. *Virology* 250, 173-84.

Locksley, R. M., Killeen, N. & Lenardo, M. J. (2001). The TNF and TNF receptor superfamilies: integrating mammalian biology. *Cell* 104, 487-501.

Loparev, V. N., Parsons, J. M., Knight, J. C., Panus, J. F., Ray, C. A., Buller, R. M., Pickup, D. J. & Esposito, J. J. (1998). A third distinct tumor necrosis factor receptor of orthopoxviruses. *Proc. Natl. Acad. Sci. U.S.A.* 95, 3786-3791.

Parry, C. M., Simas, J. P., Smith, V. P., Stewart, C. A., Minson, A. C., Efstathiou, S. & Alcami, A. (2000). A broad spectrum secreted chemokine binding protein encoded by a herpesvirus. *J. Exp. Med.* 191, 573-8.

Price, N., Tscharke, D. C., Hollinshead, M. & Smith, G. L. (2000). Vaccinia virus gene B7R encodes an 18-kDa protein that is resident in the endoplasmic reticulum and affects virus virulence. *Virology* 267, 65-79.

Reading, P. C., Symons, J. A. & Smith, G. L. (2003). A soluble chemokine-binding protein from vaccinia virus reduces virus virulence and the inflammatory response to infection. *J Immunol* 170, 1435-42.

Saraiva, M. & Alcami, A. (2001). CrmE, a novel soluble tumor necrosis factor receptor encoded by poxviruses. *J. Virol.* 75, 226-33.

Schreiber, M., Sedger, L. & McFadden, G. (1997). Distinct domains of M-T2, the myxoma virus TNF receptor homolog, mediate extracellular TNF binding and intracellular apoptosis inhibition. *J. Virol.* 71, 2171-2181.

Seet, B. T., Johnston, J. B., Brunetti, C. R., Barrett, J. W., Everett, H., Cameron, C., Sypula, J., Nazarian, S. H., Lucas, A. & McFadden, G. (2003). Poxviruses and immune evasion. *Annu Rev Immunol* 21, 377-423.

Seet, B. T. & McFadden, G. (2002). Viral chemokine-binding proteins. *J Leukoc Biol* 72, 24-34.

Smith, C. A., Hu, F. Q., Smith, T. D., Richards, C. L., Smolak, P., Goodwin, R. G. & Pickup, D. J. (1996). Cowpox virus genome encodes a second soluble homologue of cellular TNF receptors, distinct from CrmB, that binds TNF but not LT alpha. *Virology* 223, 132-147.

van Berkel, V., Barrett, J., Tiffany, H. L., Fremont, D. H., Murphy, P. M., McFadden, G., Speck, S. H. & Virgin, H. I. (2000). Identification of a gammaherpesvirus selective chemokine binding protein that inhibits chemokine action. *J. Virol.* 74, 6741-7.

Wallach, D. (2001). TNF ligand and TNF/NGF receptor families. In *Cytokine Reference*, pp. 377-412. Edited by J. Oppenheim & M. Feldman: Academic Press.

Zaballos, A., Gutierrez, J., Varona, R., Ardavin, C. & Marquez, G. (1999). Cutting edge: identification of the orphan chemokine receptor GPR-9-6 as CCR9, the receptor for the chemokine TECK. *J Immunol* 162, 5671-5.

TABLE 1

Chemokine binding proteins encoded by poxviruses and herpesviruses

| | Protein | Virus | Binding specificity | References |
|---|---|---|---|---|
| vCKBP1 | M-T7 | Poxvirus: Myxoma virus | Broad CC chemokines | (Lalani et al., 1997) (Alcami et al., 1998, Graham et al., 1997, Seet et al., 2003, Smith et al., 1997, Smith & Alcami, 2000) (Parry et al., 2000, van Berkel et al., 2000) (Bryant et al., 2003) |
| vCKBP2 | 35 kDa, M-T1, vCCI | Poxvirus: Vaccinia virus, cowpox virus, ectromelia virus, myxoma virus, variola virus, orf virus | | |
| vCKBP3 vCKBP4 | M3 gG | Gammaherpesvirus: murine gammaherpesvirus 68 Alphaherpesvirus: equine herpesvirus, bovine herpesvirus | broad broad | |

TABLE 2

Affinity constants ($K_D$) of EV E12 protein for different chemokines obtained by SPR. The purified recombinant protein was thiolcoupled to a low level and different concentrations of the indicated chemokines injected at high flow rate using a BIAcoreX. The $K_D$ for each case was determined using the BIAevaluation software.

| Chemokine | $K_D$ (nM) |
|---|---|
| mCCL21 | 0.5 |
| mCCL25 | 0.7 |
| mCCL27 | 2 |
| mCXCL11 | 1 |
| mCXCL13 | 1.5 |
| mCXCL14 | 1.5 |

TABLE 3

Recombinant plasmids prepared in order to express vTNFRs.

| Insert | Oligo | Ta | RS | Plasmid |
|---|---|---|---|---|
| pBac1 | | | | |
| EV crmD | 5' CrmD-7　3' CrmD-9 | 55 | BamHI XhoI | pMS1 |
| EV crmD-CRD 1,2 | 5' CrmD-7　3' CrmD-29 | 50 | BamHI NotI | pMS42 |
| EV crmD-CRD 1,2,3 | 5' CrmD-7　3' PT-3 | 50 | BamHI NotI | pMS46 |
| EV crmD-CRD 1,2,3,4 | 5' CrmD-7　3' PT-4 | 50 | BamHI NotI | pMS48 |
| EV crmD-CTD | 5' PT-1　3' PT-2 | 50 | NotI XhoI | pPT6 |
| EV crmD-CRD 1,2-CTD | EV crmD Ct subcloned into NotI/XhoI of pMS42 | | | pPT1 |
| EV crmD-CRD 1,2,3-CTD | EV crmD Ct subcloned into NotI/XhoI of pMS42 | | | pPT2 |
| CPV crmB-CTD | 5' PT-5　3' PT-6 | 50 | NotI XhoI | pPT5 |
| EV crmD-CRD 1,2,3,4-CPV crmB CTD | CPV crmB Ct subcloned into NotI/XhoI of pMS48 | | | pPT3 |
| CPV crmB-CRD 1,2,3,4-EV crmD CTD | 5' SF-1　3' PT-7　PMJ-601　RpMJ-601 | 50 | EcoRI NotI | pPT4 |
| EV crmD | 5' CrmD-7　3' CrmD-15 | 50 | BamHI KpnI | pMS11 |
| EV crmD-CRD 1,2 | 5' CrmD-7　3' CrmD-23 | 50 | BamHI HindIII | pMS21 |

The referred inserts were amplified by PCR from viral DNA using the indicated pair of oligonucleotides (for the oligonucleotides sequences see Table 4).
EV refers to strain Hampstead and CPV to strain Brighton Red.

TABLE 4

OLIGONUCLEOTIDES USED FOR EXPRESSION OF EV CRMD AND CPV CRMB IN THE BACULOVIRUS AND VV SYSTEMS
(SEQ ID NOS 43-57 DISCLOSED RESPECTIVELY IN ORDER OF APPEARANCE)

| Oligonucleotide | Sequence (5' > 3') |
|---|---|
| 5' CrmD-7 | CGCGTTTAAACGGATCCATGATGAAGATGACACCATCATA |
| 3' CrmD-9 | CGCCTCGAGATCTCTTTCACAATCATTTGGTGG |
| 3' CrmD-15 | CGCGGTACCTCAATCTCTTTCACAATCATTTGG |
| 3' CrmD-22 | CGCGGTACCTTAATCTATGCTGTTAAAGGACAGATCAC |
| 3' CrmD-23 | GCGAAGCTTTTACCATGGGTAGTATCCGGATGCACAGACAC |
| 3' CrmD-24 | GCGAAGCTTTTACCATGGACAAGAGGTCTTGTTAACAGGATAC |
| 3' CrmD-29 | GCGGCGGCCGCGTAGTATCCGGATGCACAGACAC |
| 5' PT-1 | GCGGCGGCCGCCAATTCGAGTATAGGAAGCAGCAGTAC |
| 3' PT-2 | GCGCTCGAGATCTCTTTCACAATCATTTGGTGG |

TABLE 4-continued

OLIGONUCLEOTIDES USED FOR EXPRESSION OF EV CRMD AND CPV CRMB IN THE BACULOVIRUS AND VV SYSTEMS
(SEQ ID NOS 43-57 DISCLOSED RESPECTIVELY IN ORDER OF APPEARANCE)
Oligonucleotide Sequence (5' > 3')

| | |
|---|---|
| 3'PT-3 | GCGGCGGCCGCATCTATGCTGTTAAAGGACAGATCAC |
| 3'PT-4 | GCGGCGGCCGCACAAGAGGTCTTGTTAACAGGATAC |
| 5'PT-5 | GCGGCGGCCGCCACTCGGACGACCACTACCGGTCTC |
| 3'PT-6 | GCGCTCGAGTAAAAAGTGGGTGGGATACTGGGAA |
| 3'PT-7 | GCGGCGGCCGCACACGATGTGTCGTTGACGGGATAC |
| 5' SF-1 | GCGGGTACCGAATTCACCATGGAGTCATATATATTGCTATTGC |

The invention claimed is:

1. An isolated C-terminal domain (CTD) from cytokine response modifier D (CrmD), wherein the CTD consists of the amino acid sequence of SEQ ID NO: 22 or consists of the amino acid sequence of SEQ ID NO: 24 and the CTD is capable of binding to chemokines and enhancing the immunomodulatory properties of viral TNF receptors.

2. A composition comprising the CTD according to claim 1 and a pharmaceutical excipient.

3. A composition according to claim 2, further comprising an immunosuppressant or anti-inflammatory substance.

4. A test kit comprising the isolated C-terminal domain (CTD) according to claim 1, wherein the CTD is labeled with immobilized reactant.

5. A fusion polypeptide comprising an isolated C-terminal domain (CTD) from cytokine response modifier D (CrmD) consisting of the amino add sequence of SEQ ID NO: 22 or consisting of the amino acid sequence of SEQ ID NO: 24, wherein the CTD is fused to a polypeptide sequence of the same or other origin and the CTD is capable of binding to chemokines and enhancing the immunomodulatory properties of viral TNF receptors.

6. A composition comprising the fusion polypeptide according to claim 5 and a pharmaceutical excipient.

7. A fusion polypeptide comprising an isolated C-terminal domain (CTD) from cytokine response modifier D (CrmD) consisting of the amino acid sequence of SEQ ID NO: 22 or consisting of the amino acid sequence of SEQ ID NO: 24, wherein the CTD is fused to an N-terminal TNF binding domain of TNFRs and the CTD is capable of binding to chemokines and enhancing the immunomodulatory properties of viral TNF receptors.

8. A fusion polypeptide according to claim 7, wherein the TNFRs are of human origin.

* * * * *

SEQUENCE LISTING

<160> NUMBER OF SEQ ID NOS: 57

<210> SEQ ID NO 1
<211> LENGTH: 963
<212> TYPE: DNA
<213> ORGANISM: Cowpox virus strain Brighton Red

<400> SEQUENCE: 1

```
atgatgaata tgacaccatc atacatcttg ttggtatata tgttcgtagt cgtaagtgga    60
gatgttcctt atgaacacat taatgggaaa tgtaacggta ccgactataa tagtaataat   120
ctatgttgta acaatgcga tcctggaatg tatatgactc attcctgtaa taccacttct   180
aatacaaaat gtgacaagtg cccagatggc acctttacat ccattcctaa tcatattccc   240
acgtgtctaa gttgtcgagg caaatgtagc agtaatcatg tagagactaa atcgtgtagt   300
aacacacagg acagagtatg tgtctgtgca tccggatact actgcgaatt tgaaggatca   360
aacggttgca ggctatgtgt accacaaaca aagtgtgatt ctggttacgg tgtatatggc   420
tactcatcta aaggagatgt aatatgtaaa agtgtccgg taatataga taatgtgat   480
ctgtccttta acagcataga tgtagaaatt aatatgtatc ctgttaacaa gacctcttgt   540
aattcgagta taggaagtag cagtaccata tcaacttccg agttaacaat tactctaaaa   600
catgaggatt gtactactgt ctttattgga gattactatt cagtcgttga taaactagca   660
acttcaggtt tctttacaaa cgataaagta catcaagacc tcacaacgca gtgcaagatt   720
aatctagaaa tcaaatgtaa ttctggagga gaatctagac aactaacacc cacgacgaag   780
gtatacttta tgcctcattc agaaacggta actgtggtag agactgtct ctctaatctc   840
gatgtctata tagtatatgc caatacggac gcgatatatt ccgacatgga tgtcgtcgct   900
tatcatacta gttatatact aaatgttgat catattccac caaatgattg tgaaagagat   960
tga                                                                963
```

<210> SEQ ID NO 2
<211> LENGTH: 320
<212> TYPE: PRT
<213> ORGANISM: Cowpox virus strain Brighton Red

<400> SEQUENCE: 2

```
Met Met Asn Met Thr Pro Ser Tyr Ile Leu Leu Val Tyr Met Phe Val
 1               5                  10                  15

Val Val Ser Gly Asp Val Pro Tyr Glu His Ile Asn Gly Lys Cys Asn
```

|            |            |            | 20         |            |            | 25         |            |            | 30         |            |            |
|---|---|---|---|---|---|---|---|---|---|---|---|

Gly Thr Asp Tyr Asn Ser Asn Asn Leu Cys Cys Lys Gln Cys Asp Pro
           35                   40                   45

Gly Met Tyr Met Thr His Ser Cys Asn Thr Thr Ser Asn Thr Lys Cys
 50                     55                   60

Asp Lys Cys Pro Asp Gly Thr Phe Thr Ser Ile Pro Asn His Ile Pro
65                  70                   75                   80

Thr Cys Leu Ser Cys Arg Gly Lys Cys Ser Ser Asn His Val Glu Thr
           85                   90                   95

Lys Ser Cys Ser Asn Thr Gln Asp Arg Val Cys Val Cys Ala Ser Gly
         100                 105               110

Tyr Tyr Cys Glu Phe Glu Gly Ser Asn Gly Cys Arg Leu Cys Val Pro
         115                 120               125

Gln Thr Lys Cys Asp Ser Gly Tyr Gly Val Tyr Gly Tyr Ser Ser Lys
    130                 135               140

Gly Asp Val Ile Cys Lys Lys Cys Pro Gly Asn Ile Asp Lys Cys Asp
145                 150                 155               160

Leu Ser Phe Asn Ser Ile Asp Val Glu Ile Asn Met Tyr Pro Val Asn
         165                 170               175

Lys Thr Ser Cys Asn Ser Ser Ile Gly Ser Ser Ser Thr Ile Ser Thr
    180                 185               190

Ser Glu Leu Thr Ile Thr Leu Lys His Glu Asp Cys Thr Thr Val Phe
         195                 200               205

Ile Gly Asp Tyr Tyr Ser Val Val Asp Lys Leu Ala Thr Ser Gly Phe
    210                 215               220

Phe Thr Asn Asp Lys Val His Gln Asp Leu Thr Thr Gln Cys Lys Ile
225                 230                 235               240

Asn Leu Glu Ile Lys Cys Asn Ser Gly Gly Ser Arg Gln Leu Thr
         245                 250               255

Pro Thr Thr Lys Val Tyr Phe Met Pro His Ser Glu Thr Val Thr Val
    260                 265               270

Val Gly Asp Cys Leu Ser Asn Leu Asp Val Tyr Ile Val Tyr Ala Asn
         275                 280               285

Thr Asp Ala Ile Tyr Ser Asp Met Asp Val Val Ala Tyr His Thr Ser
    290                 295               300

Tyr Ile Leu Asn Val Asp His Ile Pro Pro Asn Asp Cys Glu Arg Asp
305                 310                 315               320

<210> SEQ ID NO 3
<211> LENGTH: 960
<212> TYPE: DNA
<213> ORGANISM: Ectromelia virus strain Naval

<400> SEQUENCE: 3

| | | | | | |
|---|---|---|---|---|---|
| atgatgaaga | tgacaccatc | atacatcttg | ttggtatata | tgttcgtagt | cgtaagtgga | 60 |
| gatgttccgt | atacacccat | taatgggaaa | tgtaacggta | cagactataa | cagtaataat | 120 |
| ctatgttgta | aacaatgcaa | tcctggaatg | tatatgactc | attcctgtaa | taccacttct | 180 |
| aatacaaaat | gtgacaagtg | cccagatgac | acctttacat | ccattcctaa | tcatagtccc | 240 |
| gcgtgtctaa | gttgtcgagg | caaatgtagc | agtaatcaag | tagagactaa | atcgtgtagt | 300 |
| aacacacagg | acagagtatg | tgtctgtgca | tccggatact | actgcgaatt | tgaaggatca | 360 |
| aacggttgca | ggctatgtgt | accacaaaca | aagtgtggtt | ctggttacgg | tgtatatggc | 420 |
| tactcatcta | aaggagatgt | aatatgtaaa | aagtgtccgg | gtaatataga | taaatgtgat | 480 |

```
ctgtccttta acagcataga tgtagaaatt aatatgtatc ctgttaacaa gacctcttgt    540
aattcgagta taggaagcag cagtaccata tcaacttccg agttaacaat tactctaaca    600
catgaggatt gtactcctgt ctttattgga gattactatt cagtcgttga taaactagca    660
acttcaggtt tctttacaaa cgataaagta catcaagacc tcacaacgca gtgcaagatt    720
aatctagaaa tcaaatgtaa ttctggaaga gaatctagac aactaacacc cacgacgaag    780
gtatacctta tgcctcattc agaaacggta actgtggtag agactgtct ctctaatctc    840 gatgtctata tagtatatgc caatacggac gcgatatatt ccgacatgga cgtcgtcgcg    900
tatcatacta gttatatact aaatgttgat catattccac caaatgattg tgaaagagat    960
```

<210> SEQ ID NO 4
<211> LENGTH: 320
<212> TYPE: PRT
<213> ORGANISM: Ectromelia virus strain Naval

<400> SEQUENCE: 4

```
Met Met Lys Met Thr Pro Ser Tyr Ile Leu Leu Val Tyr Met Phe Val
 1               5                  10                  15

Val Val Ser Gly Asp Val Pro Tyr Thr Pro Ile Asn Gly Lys Cys Asn
            20                  25                  30

Gly Thr Asp Tyr Asn Ser Asn Asn Leu Cys Cys Lys Gln Cys Asn Pro
        35                  40                  45

Gly Met Tyr Met Thr His Ser Cys Asn Thr Thr Ser Asn Thr Lys Cys
    50                  55                  60

Asp Lys Cys Pro Asp Asp Thr Phe Thr Ser Ile Pro Asn His Ser Pro
65                  70                  75                  80

Ala Cys Leu Ser Cys Arg Gly Lys Cys Ser Ser Asn Gln Val Glu Thr
                85                  90                  95

Lys Ser Cys Ser Asn Thr Gln Asp Arg Val Cys Val Cys Ala Ser Gly
            100                 105                 110

Tyr Tyr Cys Glu Phe Glu Gly Ser Asn Gly Cys Arg Leu Cys Val Pro
        115                 120                 125

Gln Thr Lys Cys Gly Ser Gly Tyr Gly Val Tyr Gly Tyr Ser Ser Lys
    130                 135                 140

Gly Asp Val Ile Cys Lys Lys Cys Pro Gly Asn Ile Asp Lys Cys Asp
145                 150                 155                 160

Leu Ser Phe Asn Ser Ile Asp Val Glu Ile Asn Met Tyr Pro Val Asn
                165                 170                 175

Lys Thr Ser Cys Asn Ser Ser Ile Gly Ser Ser Thr Ile Ser Thr
            180                 185                 190

Ser Glu Leu Thr Ile Thr Leu Thr His Glu Asp Cys Thr Pro Val Phe
        195                 200                 205

Ile Gly Asp Tyr Tyr Ser Val Val Asp Lys Leu Ala Thr Ser Gly Phe
    210                 215                 220

Phe Thr Asn Asp Lys Val His Gln Asp Leu Thr Thr Gln Cys Lys Ile
225                 230                 235                 240

Asn Leu Glu Ile Lys Cys Asn Ser Gly Arg Glu Ser Arg Gln Leu Thr
                245                 250                 255

Pro Thr Thr Lys Val Tyr Leu Met Pro His Ser Glu Thr Val Thr Val
            260                 265                 270

Val Gly Asp Cys Leu Ser Asn Leu Asp Val Tyr Ile Val Tyr Ala Asn
        275                 280                 285
```

```
Thr Asp Ala Ile Tyr Ser Asp Met Asp Val Val Ala Tyr His Thr Ser
    290             295             300
Tyr Ile Leu Asn Val Asp His Ile Pro Pro Asn Asp Cys Glu Arg Asp
305             310             315             320

<210> SEQ ID NO 5
<211> LENGTH: 609
<212> TYPE: DNA
<213> ORGANISM: Ectromelia virus strain Naval

<400> SEQUENCE: 5
atgataaaca taaacataaa cacaatacta atattcgcat cattatttgt tgcatcgttt     60
gcaaatgatt atcctccacc cggtttcttc gaaaacaaat acattacaga tacatttaat    120
tacatatcta tagattttga actatatcca gttaacgtat catcttgtaa tcgactaagt    180
acaaaacaat catccgatat tatcacgact tctgaattaa caattactgt taatagtaca    240
gactgcgatc cagtctttgt aacagaatat tattctgtaa aggataaaac tgctgtagcc    300 ggactttca cagatactac aaaaaaacaa aatacatcca gatgtgtac gctgaatgta    360 gaagtaaaat gtaacgctga aacggaacct gtattaatcg gtaattttac acgtgttcct    420
gaaacagcat caacccacgc tgaaaatttc actttaatag gcaactgtct atcagatctc    480
catctctata ttgcgtacgt caataccgat gagggatttg aagaggatac tgctactatt    540
catataggaa acatgatcga tattagcggg ataccctcca aatacttgcgc tactagaact    600 attaattag                                                             609

<210> SEQ ID NO 6
<211> LENGTH: 202
<212> TYPE: PRT
<213> ORGANISM: Ectromelia virus strain Naval

<400> SEQUENCE: 6

Met Ile Asn Ile Asn Ile Asn Thr Ile Leu Ile Phe Ala Ser Leu Phe
  1               5                  10                  15

Val Ala Ser Phe Ala Asn Asp Tyr Pro Pro Gly Phe Phe Glu Asn
             20                  25                  30

Lys Tyr Ile Thr Asp Thr Phe Asn Tyr Ile Ser Ile Asp Phe Glu Leu
         35                  40                  45

Tyr Pro Val Asn Val Ser Ser Cys Asn Arg Leu Ser Thr Lys Gln Ser
     50                  55                  60

Ser Asp Ile Ile Thr Thr Ser Glu Leu Thr Ile Thr Val Asn Ser Thr
 65                  70                  75                  80

Asp Cys Asp Pro Val Phe Val Thr Glu Tyr Tyr Ser Val Lys Asp Lys
                 85                  90                  95

Thr Ala Val Ala Gly Leu Phe Thr Asp Thr Thr Lys Lys Gln Asn Thr
            100                 105                 110

Ser Lys Met Cys Thr Leu Asn Val Glu Val Lys Cys Asn Ala Glu Thr
        115                 120                 125

Glu Pro Val Leu Ile Gly Asn Phe Thr Arg Val Pro Glu Thr Ala Ser
    130                 135                 140

Thr His Ala Glu Asn Phe Thr Leu Ile Gly Asn Cys Leu Ser Asp Leu
145                 150                 155                 160

His Leu Tyr Ile Ala Tyr Val Asn Thr Asp Glu Gly Phe Glu Glu Asp
                165                 170                 175

Thr Ala Thr Ile His Ile Gly Asn Met Ile Asp Ile Ser Gly Ile Pro
            180                 185                 190
```

Pro Asn Thr Cys Ala Thr Arg Thr Ile Asn
        195                 200

<210> SEQ ID NO 7
<211> LENGTH: 609
<212> TYPE: DNA
<213> ORGANISM: Cowpox virus strain Brighton Red

<400> SEQUENCE: 7
atgataaaca taaacataaa cacaatacta atattcgcat cattatttgt tgcatcgttt      60
gcaaatgatt atcctccacc cggtttcttc gaagacaaat acattacaaa tacatttaac    120
tacatatcta tagattttga actatatcca gttaacgtat catcttgtaa tcgactaagt    180
acaaaacaat catcagatgt tatatcgact tctgaattga caattactgt taatagtaca    240
gattgtgatc cagtctttgt aacagaatat tactctgtaa aggataaaac tgctatagcc    300
ggactttca cagatactac aaaaaaacaa aatacatcca agatgtgtac gctgaatata    360
gaagtaaaat gtaacgctga aacggaacct gtattaatcg gtaattttac acgcgttcct    420
gaaaaagcat caacacacgc tgaaaatttc actttaatag caactgtct atcagatctc    480
catctctata ttgcgtatgt caataccgat gaggaatttg aagaggatac tgctactgtt    540
catataggaa acaaactcga tattaacggt atacctccaa atatgtgcgc taccagaacc    600
attaattag                                                            609

<210> SEQ ID NO 8
<211> LENGTH: 202
<212> TYPE: PRT
<213> ORGANISM: Cowpox virus strain Brighton Red

<400> SEQUENCE: 8

Met Ile Asn Ile Asn Ile Asn Thr Ile Leu Ile Phe Ala Ser Leu Phe
  1               5                  10                  15

Val Ala Ser Phe Ala Asn Asp Tyr Pro Pro Gly Phe Phe Glu Asp
             20                  25                  30

Lys Tyr Ile Thr Asn Thr Phe Asn Tyr Ile Ser Ile Asp Phe Glu Leu
         35                  40                  45

Tyr Pro Val Asn Val Ser Ser Cys Asn Arg Leu Ser Thr Lys Gln Ser
     50                  55                  60

Ser Asp Val Ile Ser Thr Ser Glu Leu Thr Ile Thr Val Asn Ser Thr
 65                  70                  75                  80

Asp Cys Asp Pro Val Phe Val Thr Glu Tyr Tyr Ser Val Lys Asp Lys
                 85                  90                  95

Thr Ala Ile Ala Gly Leu Phe Thr Asp Thr Thr Lys Lys Gln Asn Thr
            100                 105                 110

Ser Lys Met Cys Thr Leu Asn Ile Glu Val Lys Cys Asn Ala Glu Thr
        115                 120                 125

Glu Pro Val Leu Ile Gly Asn Phe Thr Arg Val Pro Glu Lys Ala Ser
    130                 135                 140

Thr His Ala Glu Asn Phe Thr Leu Ile Gly Asn Cys Leu Ser Asp Leu
145                 150                 155                 160

His Leu Tyr Ile Ala Tyr Val Asn Thr Asp Glu Glu Phe Glu Glu Asp
                165                 170                 175

Thr Ala Thr Val His Ile Gly Asn Lys Leu Asp Ile Asn Gly Ile Pro
            180                 185                 190

Pro Asn Met Cys Ala Thr Arg Thr Ile Asn
        195                 200

<210> SEQ ID NO 9
<211> LENGTH: 1047
<212> TYPE: DNA
<213> ORGANISM: Variola major virus strain Bangladesh

<400> SEQUENCE: 9

```
atgaagtccg tattatactt gtatatattg tttctctcat gtataataaa cggaagagat      60
gcagcaccgt ataccaccc caatggaaag tgtaaagaca ccgaatacaa acgccataat     120
ctgtgttgtt tatcgtgtcc tccgggaaca tacgcttcca gattatgtga tagcaagact     180
aacacacaat gtaccccgtg tggttcgggt acctttacat ctcgcaataa tcatttaccc     240
gcttgtctaa gttgtaacgg aagatgcaat agtaatcagg tagagacgcg atcgtgtaac     300
acgactcaca atagaatctg tgaatgctct cccggatatt attgtcttct aaaggatca      360
tccggatgca aggcatgtgt tcccaaaca aaatgtggaa taggatacgg agtatccgga     420
cacacgtctg ttggagacgt catctgttct ccgtgtggtt cggaacata ttctcacacc      480
gtctcttccg cagataaatg cgaacccgta cccaacaata catttaacta tatcgatgtg     540
gaaattacac tgtatccagt taacgacaca tcgtgtactc ggacgaccac taccggtctc     600
agcgaatcca tcttaacgtc ggaactaact attactatga atcatacaga ttgcaatccc     660
gtatttcgtg aggaatactt ctctgtcctt aataaggtag caacttcagg attttttaca     720
ggagaaaata gatatcaaaa tatttcaaag gtgtgtactt taaattttga gattaaatgt     780
aataacaaag gttcttcctt caaacagcta acgaaagcaa agaatgatga cggtatgatg     840
tcgcattcgg agacggtaac tctagcgggt gactgtctat ctagcgtcga catctatata     900
ctatatagta ataccaatgc tcaagactac gaaactgata caatctctta tcgtgtgggt     960
aatgttctcg atgatgatag ccatatgccc ggtagttgca atatacataa accgatcact    1020
aattccaaac ccacccgctt tttatag                                        1047
```

<210> SEQ ID NO 10
<211> LENGTH: 348
<212> TYPE: PRT
<213> ORGANISM: Variola major virus strain Bangladesh

<400> SEQUENCE: 10

```
Met Lys Ser Val Leu Tyr Leu Tyr Ile Leu Phe Leu Ser Cys Ile Ile
  1               5                  10                  15

Asn Gly Arg Asp Ala Ala Pro Tyr Thr Pro Pro Asn Gly Lys Cys Lys
             20                  25                  30

Asp Thr Glu Tyr Lys Arg His Asn Leu Cys Cys Leu Ser Cys Pro Pro
         35                  40                  45

Gly Thr Tyr Ala Ser Arg Leu Cys Asp Ser Lys Thr Asn Thr Gln Cys
     50                  55                  60

Thr Pro Cys Gly Ser Gly Thr Phe Thr Ser Arg Asn Asn His Leu Pro
 65                  70                  75                  80

Ala Cys Leu Ser Cys Asn Gly Arg Cys Asn Ser Asn Gln Val Glu Thr
                 85                  90                  95

Arg Ser Cys Asn Thr Thr His Asn Arg Ile Cys Glu Cys Ser Pro Gly
            100                 105                 110

Tyr Tyr Cys Leu Leu Lys Gly Ser Ser Gly Cys Lys Ala Cys Val Ser
        115                 120                 125

Gln Thr Lys Cys Gly Ile Gly Tyr Gly Val Ser Gly His Thr Ser Val
```

```
              130                 135                 140
Gly Asp Val Ile Cys Ser Pro Cys Gly Phe Gly Thr Tyr Ser His Thr
145                 150                 155                 160

Val Ser Ser Ala Asp Lys Cys Glu Pro Val Pro Asn Asn Thr Phe Asn
                165                 170                 175

Tyr Ile Asp Val Glu Ile Thr Leu Tyr Pro Val Asn Asp Thr Ser Cys
                180                 185                 190

Thr Arg Thr Thr Thr Thr Gly Leu Ser Glu Ser Ile Leu Thr Ser Glu
                195                 200                 205

Leu Thr Ile Thr Met Asn His Thr Asp Cys Asn Pro Val Phe Arg Glu
            210                 215                 220

Glu Tyr Phe Ser Val Leu Asn Lys Val Ala Thr Ser Gly Phe Phe Thr
225                 230                 235                 240

Gly Glu Asn Arg Tyr Gln Asn Ile Ser Lys Val Cys Thr Leu Asn Phe
                245                 250                 255

Glu Ile Lys Cys Asn Asn Lys Gly Ser Ser Phe Lys Gln Leu Thr Lys
                260                 265                 270

Ala Lys Asn Asp Asp Gly Met Met Ser His Ser Glu Thr Val Thr Leu
            275                 280                 285

Ala Gly Asp Cys Leu Ser Ser Val Asp Ile Tyr Ile Leu Tyr Ser Asn
290                 295                 300

Thr Asn Ala Gln Asp Tyr Glu Thr Asp Thr Ile Ser Tyr Arg Val Gly
305                 310                 315                 320

Asn Val Leu Asp Asp Asp Ser His Met Pro Gly Ser Cys Asn Ile His
                325                 330                 335

Lys Pro Ile Thr Asn Ser Lys Pro Thr Arg Phe Leu
                340                 345

<210> SEQ ID NO 11
<211> LENGTH: 1068
<212> TYPE: DNA
<213> ORGANISM: Cowpox virus strain Brighton Red

<400> SEQUENCE: 11
atgaagtcat atatattgct attgctgctt tcatgtataa tcataataaa cagcgatata      60
acaccgcatg aaccatccaa cggaaagtgt aaagacaacg aatacaaacg ccatcatcta     120
tgttgtttat cgtgtcctcc gggaacatac gcttccagat tatgcgatag caagactaac     180
acaaacacac aatgtacgcc gtgtgcgtcg gacacccttta cgtctcgcaa taatcattta     240
cccgcttgtc taagttgtaa cggaagatgc gatagtaatc aggtagagac gcgatcgtgt     300
aacacgactc acaatagaat ctgtgattgt gctcccggat attattgttt tctcaaagga     360
tcatccggat gcaaggcatg tgtttcccaa acaaagtgtg aataggata cggagtatcc     420 ggacacacgc taccggaga cgtcgtctgt tctccgtgtg gtctcggaac atattctcac     480
accgtctctt ccgtagataa atgcgaaccc gtacccagta ataccttttaa ctatatcgat     540 gtggaaatta atctgtatcc cgtcaacgac acatcgtgta ctcggacgac cactaccggt     600
ctcagtgaat ccatctcaac ttcggaacta acgattacta tgaatcataa agactgcgat     660
cccgtctttc gtaatggata cttctccgtt cttaatgagg tagcaacttc agggttcttt     720
acaggacaaa atagatatca gaatatttca aaggtatgca ctctgaattt cgagattaaa     780
tgtaataaca agattcttat ttcttcctcc aaacagttaa cgaaaacaaa gaatgatgac     840
gactccatca tgccgcattc ggaatcggta actctagtgg gcgactgtct atccagcgtc     900
```

```
gacatctata tactatatag taataccaat actcaagact acgaaactga tacaatctct    960
tatcatgtgg gtaatgttct cgatgtcgat agccatatgc ccggtaggtg cgatacacat   1020
aaactgatta ctaattccaa ttcccagtat cccacccact ttttatag                1068
```

<210> SEQ ID NO 12  
<211> LENGTH: 355  
<212> TYPE: PRT  
<213> ORGANISM: Cowpox virus strain Brighton Red
<400> SEQUENCE: 12

```
Met Lys Ser Tyr Ile Leu Leu Leu Leu Ser Cys Ile Ile Ile
  1               5                  10                  15

Asn Ser Asp Ile Thr Pro His Glu Pro Ser Asn Gly Lys Cys Lys Asp
                 20                  25                  30

Asn Glu Tyr Lys Arg His His Leu Cys Cys Leu Ser Cys Pro Pro Gly
             35                  40                  45

Thr Tyr Ala Ser Arg Leu Cys Asp Ser Lys Thr Asn Thr Asn Thr Gln
 50                  55                  60

Cys Thr Pro Cys Ala Ser Asp Thr Phe Thr Ser Arg Asn Asn His Leu
 65                  70                  75                  80

Pro Ala Cys Leu Ser Cys Asn Gly Arg Cys Asp Ser Asn Gln Val Glu
                 85                  90                  95

Thr Arg Ser Cys Asn Thr Thr His Asn Arg Ile Cys Asp Cys Ala Pro
            100                 105                 110

Gly Tyr Tyr Cys Phe Leu Lys Gly Ser Ser Gly Cys Lys Ala Cys Val
            115                 120                 125

Ser Gln Thr Lys Cys Gly Ile Gly Tyr Gly Val Ser Gly His Thr Pro
130                 135                 140

Thr Gly Asp Val Val Cys Ser Pro Cys Gly Leu Gly Tyr Ser His
145                 150                 155                 160

Thr Val Ser Ser Val Asp Lys Cys Glu Pro Val Pro Ser Asn Thr Phe
                165                 170                 175

Asn Tyr Ile Asp Val Glu Ile Asn Leu Tyr Pro Val Asn Asp Thr Ser
            180                 185                 190

Cys Thr Arg Thr Thr Thr Thr Gly Leu Ser Glu Ser Ile Ser Thr Ser
            195                 200                 205

Glu Leu Thr Ile Thr Met Asn His Lys Asp Cys Asp Pro Val Phe Arg
210                 215                 220

Asn Gly Tyr Phe Ser Val Leu Asn Glu Val Ala Thr Ser Gly Phe Phe
225                 230                 235                 240

Thr Gly Gln Asn Arg Tyr Gln Asn Ile Ser Lys Val Cys Thr Leu Asn
                245                 250                 255

Phe Glu Ile Lys Cys Asn Asn Lys Asp Ser Tyr Ser Ser Lys Gln
            260                 265                 270

Leu Thr Lys Thr Lys Asn Asp Asp Ser Ile Met Pro His Ser Glu
            275                 280                 285

Ser Val Thr Leu Val Gly Asp Cys Leu Ser Ser Val Asp Ile Tyr Ile
290                 295                 300

Leu Tyr Ser Asn Thr Asn Thr Gln Asp Tyr Glu Thr Thr Ile Ser
305                 310                 315                 320

Tyr His Val Gly Asn Val Leu Asp Val Asp Ser His Met Pro Gly Arg
                325                 330                 335

Cys Asp Thr His Lys Leu Ile Thr Asn Ser Asn Ser Gln Tyr Pro Thr
            340                 345                 350
```

His Phe Leu
    355

<210> SEQ ID NO 13
<211> LENGTH: 582
<212> TYPE: DNA
<213> ORGANISM: Cowpox virus strain Brighton Red

<400> SEQUENCE: 13

```
atgatgatat acggattaat agcctgtctt atattc

<210> SEQ ID NO 15
<211> LENGTH: 573
<212> TYPE: DNA
<213> ORGANISM: Vaccinia virus strain Western Reserve

<400> SEQUENCE: 15

```
atgatgatat acggattaat agcgtgtctt atattcgtga cttcatccat cgctagtcca    60
ctttatattc ccgttattcc acccatttcg gaagataaat cgttcaatag tgtagaggta   120
ttagtttcct tgtttagaga tgaccaaaaa gactatacgg taacttctca gttcaataac   180
tacactatcg ataccaaaga ctggactatc ggcgtactat ccacacctga tggtttggat   240
ataccattga ctaatataac ttattggtca cggtttacta taggtcgtgc attgttcaaa   300
tcagagtctg aggatatttt ccaaaagaaa atgagtattc taggtgtttc tatagaatgt   360
aagaagtcgt cgacattact tactttttg accgtgcgta aaatgactcg agtatttaat   420
aaatttccag atatggctta ttatcgagga gactgtttaa aagccgttta tgtaacaatg   480
acttataaaa atactaaaac tggagagact gattacacgt acctctctaa tggggggttg   540
cctgcatact atcgtaatgg ggtcgatggt tga                                573
```

<210> SEQ ID NO 16
<211> LENGTH: 190
<212> TYPE: PRT
<213> ORGANISM: Vaccinia virus strain Western Reserve

<400> SEQUENCE: 16

```
Met Met Ile Tyr Gly Leu Ile Ala Cys Leu Ile Phe Val Thr Ser Ser
  1               5                  10                  15

Ile Ala Ser Pro Leu Tyr Ile Pro Val Ile Pro Ile Ser Glu Asp
              20                  25                  30

Lys Ser Phe Asn Ser Val Glu Val Leu Val Ser Leu Phe Arg Asp Asp
              35                  40                  45

Gln Lys Asp Tyr Thr Val Thr Ser Gln Phe Asn Asn Tyr Thr Ile Asp
       50                  55                  60

Thr Lys Asp Trp Thr Ile Gly Val Leu Ser Thr Pro Asp Gly Leu Asp
 65                  70                  75                  80

Ile Pro Leu Thr Asn Ile Thr Tyr Trp Ser Arg Phe Thr Ile Gly Arg
                 85                  90                  95

Ala Leu Phe Lys Ser Glu Ser Glu Asp Ile Phe Gln Lys Lys Met Ser
             100                 105                 110

Ile Leu Gly Val Ser Ile Glu Cys Lys Lys Ser Ser Thr Leu Leu Thr
             115                 120                 125

Phe Leu Thr Val Arg Lys Met Thr Arg Val Phe Asn Lys Phe Pro Asp
         130                 135                 140

Met Ala Tyr Tyr Arg Gly Asp Cys Leu Lys Ala Val Tyr Val Thr Met
145                 150                 155                 160

Thr Tyr Lys Asn Thr Lys Thr Gly Glu Thr Asp Tyr Thr Tyr Leu Ser
                 165                 170                 175

Asn Gly Gly Leu Pro Ala Tyr Tyr Arg Asn Gly Val Asp Gly
             180                 185                 190
```

<210> SEQ ID NO 17
<211> LENGTH: 549
<212> TYPE: DNA
<213> ORGANISM: Vaccinia virus strain Western Reserve

<400> SEQUENCE: 17

```
atgtataaaa aactaataac gttttattt gtaataggtg cattagcatc ctattcgaat      60
aatgagtaca ctccgtttaa taaactgagt gtaaaactct atatagatgg agtagataat    120
atagaaaatt catatactga tgataataat gaattggtgt taaattttaa agagtacaca    180
atttctatta ttacagagtc atgcgacgtc ggatttgatt ccatagatat agatgttata    240
aacgactata aaattattga tatgtatacc attgactcgt ctactattca acgcagaggt    300
cacacgtgta gaatatctac caaattatca tgccattatg ataagtaccc ttatattcac    360
aaatatgatg gtgatgagcg acaatattct attactgcag agggaaaatg ctataaagga    420
ataaaatatg aaataagtat gatcaacgat gatactctat tgagaaaaca tactcttaaa    480
attggatcta cttatatatt tgatcgtcat ggacatagta atacatatta ttcaaaatat    540
gatttttaa                                                            549
```

<210> SEQ ID NO 18
<211> LENGTH: 182
<212> TYPE: PRT
<213> ORGANISM: Vaccinia virus strain Western Reserve

<400> SEQUENCE: 18

```
Met Tyr Lys Lys Leu Ile Thr Phe Leu Phe Val Ile Gly Ala Leu Ala
  1               5                  10                  15

Ser Tyr Ser Asn Asn Glu Tyr Thr Pro Phe Asn Lys Leu Ser Val Lys
             20                  25                  30

Leu Tyr Ile Asp Gly Val Asp Asn Ile Glu Asn Ser Tyr Thr Asp Asp
         35                  40                  45

Asn Glu Leu Val Leu Asn Phe Lys Glu Tyr Thr Ile Ser Ile Ile
     50                  55                  60

Thr Glu Ser Cys Asp Val Gly Phe Asp Ser Ile Asp Ile Asp Val Ile
 65                  70                  75                  80

Asn Asp Tyr Lys Ile Ile Asp Met Tyr Thr Ile Asp Ser Ser Thr Ile
                 85                  90                  95

Gln Arg Arg Gly His Thr Cys Arg Ile Ser Thr Lys Leu Ser Cys His
            100                 105                 110

Tyr Asp Lys Tyr Pro Tyr Ile His Lys Tyr Asp Gly Asp Glu Arg Gln
        115                 120                 125

Tyr Ser Ile Thr Ala Glu Gly Lys Cys Tyr Lys Gly Ile Lys Tyr Glu
    130                 135                 140

Ile Ser Met Ile Asn Asp Asp Thr Leu Leu Arg Lys His Thr Leu Lys
145                 150                 155                 160

Ile Gly Ser Thr Tyr Ile Phe Asp Arg His Gly His Ser Asn Thr Tyr
                165                 170                 175

Tyr Ser Lys Tyr Asp Phe
            180
```

<210> SEQ ID NO 19
<211> LENGTH: 546
<212> TYPE: DNA
<213> ORGANISM: Ectromelia virus strain Naval

<400> SEQUENCE: 19

```
atgtataaaa aactaataac gttttattt gtaataggtg cagtagcatc ttattcgaat      60
aatgagtaca ctccgtttaa taaacttagt gtaaaactgt atatagatgg agtagataat    120
atagaaaatt catatactga taataatgaa ttggtgttaa attttaaaga gtacacaatt    180
tctattatta cagagtcatg cgacgtcgga tttgattcca tagatataga tgttataaac    240
```

```
gactataaaa ttcttgatat gtataccatt gactcgtcta ccattcaacg cagaggtcac    300
acatgcaaaa tatctaccaa attatcatgc cattatgata agcacccttta tattcacaaa    360 tatgagggtg atgagcgaca atattctatt actgcagagg gaaaatgcta taaggaata     420 aaatatgaaa taagtatgat gcacgatgat acgctattga gaaacatac tcttaaaatt     480 ggatctactt atatattcga tcgccatgga catagtaata catattattc aaaatatgat    540
ttttaa                                                                546
```

<210> SEQ ID NO 20
<211> LENGTH: 181
<212> TYPE: PRT
<213> ORGANISM: Ectromelia virus strain Naval

<400> SEQUENCE: 20

```
Met Tyr Lys Lys Leu Ile Thr Phe Leu Phe Val Ile Gly Ala Val Ala
 1               5                  10                  15

Ser Tyr Ser Asn Asn Glu Tyr Thr Pro Phe Asn Lys Leu Ser Val Lys
            20                  25                  30

Leu Tyr Ile Asp Gly Val Asp Asn Ile Glu Asn Ser Tyr Thr Asp Asn
        35                  40                  45

Asn Glu Leu Val Leu Asn Phe Lys Glu Tyr Thr Ile Ser Ile Ile Thr
    50                  55                  60

Glu Ser Cys Asp Val Gly Phe Asp Ser Ile Asp Ile Asp Val Ile Asn
65                  70                  75                  80

Asp Tyr Lys Ile Leu Asp Met Tyr Thr Ile Asp Ser Ser Thr Ile Gln
                85                  90                  95

Arg Arg Gly His Thr Cys Lys Ile Ser Thr Lys Leu Ser Cys His Tyr
            100                 105                 110

Asp Lys His Pro Tyr Ile His Lys Tyr Glu Gly Asp Glu Arg Gln Tyr
        115                 120                 125

Ser Ile Thr Ala Glu Gly Lys Cys Tyr Lys Gly Ile Lys Tyr Glu Ile
    130                 135                 140

Ser Met Met His Asp Asp Thr Leu Leu Arg Lys His Thr Leu Lys Ile
145                 150                 155                 160

Gly Ser Thr Tyr Ile Phe Asp Arg His Gly His Ser Asn Thr Tyr Tyr
                165                 170                 175

Ser Lys Tyr Asp Phe
            180
```

<210> SEQ ID NO 21
<211> LENGTH: 480
<212> TYPE: DNA
<213> ORGANISM: Cowpox virus strain Brighton Red

<400> SEQUENCE: 21

```
tcctttaaca gcatagatgt agaaattaat atgtatcctg ttaacaagac ctcttgtaat     60
tcgagtatag gaagtagcag taccatatca acttccgagt taacaattac tctaaaacat    120
gaggattgta ctactgtctt tattggagat tactattcag tcgttgataa actagcaact    180
tcaggtttct ttcaaacga taagtacat caagacctca caacgcagtg caagattaat      240
ctagaaatca aatgtaattc tggaggagaa tctagacaac taacacccac gacgaaggta    300
tactttatgc ctcattcaga aacggtaact gtggtaggag actgtctctc taatctcgat    360
gtctatatag tatatgccaa tacggacgcg atatattccg acatggatgt cgtcgcttat    420
``` cataotagtt atataotaaa tgttgatcat attccaccaa atgattgtga aagagattga    480

<210> SEQ ID NO 22
<211> LENGTH: 159
<212> TYPE: PRT
<213> ORGANISM: Cowpox virus strain Brighton Red

<400> SEQUENCE: 22

Ser Phe Asn Ser Ile Asp Val Glu Ile Asn Met Tyr Pro Val Asn Lys
 1               5                  10                  15

Thr Ser Cys Asn Ser Ser Ile Gly Ser Ser Ser Thr Ile Ser Thr Ser
            20                  25                  30

Glu Leu Thr Ile Thr Leu Lys His Glu Asp Cys Thr Thr Val Phe Ile
        35                  40                  45

Gly Asp Tyr Tyr Ser Val Val Asp Lys Leu Ala Thr Ser Gly Phe Phe
    50                  55                  60

Thr Asn Asp Lys Val His Gln Asp Leu Thr Thr Gln Cys Lys Ile Asn
65                  70                  75                  80

Leu Glu Ile Lys Cys Asn Ser Gly Gly Glu Ser Arg Gln Leu Thr Pro
                85                  90                  95

Thr Thr Lys Val Tyr Phe Met Pro His Ser Glu Thr Val Thr Val Val
            100                 105                 110

Gly Asp Cys Leu Ser Asn Leu Asp Val Tyr Ile Val Tyr Ala Asn Thr
        115                 120                 125

Asp Ala Ile Tyr Ser Asp Met Asp Val Val Ala Tyr His Thr Ser Tyr
    130                 135                 140

Ile Leu Asn Val Asp His Ile Pro Pro Asn Asp Cys Glu Arg Asp
145                 150                 155

<210> SEQ ID NO 23
<211> LENGTH: 477
<212> TYPE: DNA
<213> ORGANISM: Ectromelia virus strain Naval

<400> SEQUENCE: 23
tcctttaaca gcatagatgt agaaattaat atgtatcctg ttaacaagac ctcttgtaat    60
tcgagtatag gaagcagcag taccatatca acttccgagt taacaattac tctaacacat   120
gaggattgta ctcctgtctt tattggagat tactattcag tcgttgataa actagcaact   180
tcaggtttct ttacaaacga taagtacat caagacctca aacgcagtg caagattaat    240 ctagaaatca aatgtaattc tggaagagaa tctagacaac taacacccac gacgaaggta   300
taccttatgc ctcattcaga aacggtaact gtggtaggag actgtctctc taatctcgat   360
gtctatatag tatatgccaa tacgacgcg atatattccg acatggacgt cgtcgcgtat    420
catactagtt atatactaaa tgttgatcat attccaccaa atgattgtga aagagat      477

<210> SEQ ID NO 24
<211> LENGTH: 159
<212> TYPE: PRT
<213> ORGANISM: Ectromelia virus strain Naval

<400> SEQUENCE: 24

Ser Phe Asn Ser Ile Asp Val Glu Ile Asn Met Tyr Pro Val Asn Lys
 1               5                  10                  15

Thr Ser Cys Asn Ser Ser Ile Gly Ser Ser Ser Thr Ile Ser Thr Ser
            20                  25                  30

Glu Leu Thr Ile Thr Leu Thr His Glu Asp Cys Thr Pro Val Phe Ile

```
                35                  40                  45
Gly Asp Tyr Tyr Ser Val Val Asp Lys Leu Ala Thr Ser Gly Phe Phe
         50                  55                  60
Thr Asn Asp Lys Val His Gln Asp Leu Thr Thr Gln Cys Lys Ile Asn
 65                  70                  75                  80
Leu Glu Ile Lys Cys Asn Ser Gly Arg Glu Ser Arg Gln Leu Thr Pro
                 85                  90                  95
Thr Thr Lys Val Tyr Leu Met Pro His Ser Glu Thr Val Thr Val Val
            100                 105                 110
Gly Asp Cys Leu Ser Asn Leu Asp Val Tyr Ile Val Tyr Ala Asn Thr
        115                 120                 125
Asp Ala Ile Tyr Ser Asp Met Asp Val Val Ala Tyr His Thr Ser Tyr
130                 135                 140
Ile Leu Asn Val Asp His Ile Pro Pro Asn Asp Cys Glu Arg Asp
145                 150                 155
```

<210> SEQ ID NO 25
<211> LENGTH: 546
<212> TYPE: DNA
<213> ORGANISM: Cowpox virus strain Brighton Red

<400> SEQUENCE: 25

```
acctttaact atatcgatgt ggaaattaat ctgtatcccg tcaacgacac atcgtgtact      60
cggacgacca ctaccggtct cagtgaatcc atctcaactt cggaactaac gattactatg     120
aatcataaag actgcgatcc cgtctttcgt aatggatact tctccgttct taatgaggta     180
gcaacttcag ggttctttac aggacaaaat agatatcaga atatttcaaa ggtatgcact     240
ctgaatttcg agattaaatg taataacaaa gattcttatt cttcctccaa acagttaacg     300
aaaacaaaga atgatgacga ctccatcatg ccgcattcgg aatcggtaac tctagtgggc     360
gactgtctat ccagcgtcga catctatata ctatatagta ataccaatac tcaagactac     420
gaaactgata caatctctta tcatgtgggt aatgttctcg atgtcgatag ccatatgccc     480
ggtaggtgcg atacacataa actgattact aattccaatt cccagtatcc cacccacttt     540
ttatag                                                                546
```

<210> SEQ ID NO 26
<211> LENGTH: 181
<212> TYPE: PRT
<213> ORGANISM: Cowpox virus strain Brighton Red

<400> SEQUENCE: 26

```
Thr Phe Asn Tyr Ile Asp Val Glu Ile Asn Leu Tyr Pro Val Asn Asp
  1               5                  10                  15
Thr Ser Cys Thr Arg Thr Thr Thr Gly Leu Ser Glu Ser Ile Ser
             20                  25                  30
Thr Ser Glu Leu Thr Ile Thr Met Asn His Lys Asp Cys Asp Pro Val
         35                  40                  45
Phe Arg Asn Gly Tyr Phe Ser Val Leu Asn Glu Val Ala Thr Ser Gly
     50                  55                  60
Phe Phe Thr Gly Gln Asn Arg Tyr Gln Asn Ile Ser Lys Val Cys Thr
 65                  70                  75                  80
Leu Asn Phe Glu Ile Lys Cys Asn Asn Lys Asp Ser Tyr Ser Ser Ser
                 85                  90                  95
Lys Gln Leu Thr Lys Thr Lys Asn Asp Asp Ser Ile Met Pro His
            100                 105                 110
```

```
Ser Glu Ser Val Thr Leu Val Gly Asp Cys Leu Ser Ser Val Asp Ile
        115                 120                 125

Tyr Ile Leu Tyr Ser Asn Thr Asn Thr Gln Asp Tyr Glu Thr Asp Thr
    130                 135                 140

Ile Ser Tyr His Val Gly Asn Val Leu Asp Val Asp Ser His Met Pro
145                 150                 155                 160

Gly Arg Cys Asp Thr His Lys Leu Ile Thr Asn Ser Asn Ser Gln Tyr
                165                 170                 175

Pro Thr His Phe Leu
            180

<210> SEQ ID NO 27
<211> LENGTH: 528
<212> TYPE: DNA
<213> ORGANISM: Variola major virus strain Bangladesh

<400> SEQUENCE: 27
acatttaact atatcgatgt ggaaattaca ctgtatccag ttaacgacac atcgtgtact    60
cggacgacca ctaccggtct cagcgaatcc atcttaacgt cggaactaac tattactatg   120
aatcatacag attgcaatcc cgtatttcgt gaggaatact ctctgtcct  aataaggta    180 gcaacttcag gatttttac aggagaaaat agatatcaaa atatttcaaa ggtgtgtact   240
ttaaattttg agattaaatg taataacaaa ggttcttcct tcaaacagct aacgaaagca   300
aagaatgatg acggtatgat gtcgcattcg agacggtaa ctctagcggg tgactgtcta   360
tctagcgtcg acatctatat actatatagt aataccaatg ctcaagacta cgaaactgat   420
acaatctctt atcgtgtggg taatgttctc gatgatgata gccatatgcc cggtagttgc   480
aatatacata aaccgatcac taattccaaa cccacccgct ttttatag                528

<210> SEQ ID NO 28
<211> LENGTH: 175
<212> TYPE: PRT
<213> ORGANISM: Variola major virus strain Bangladesh

<400> SEQUENCE: 28

Thr Phe Asn Tyr Ile Asp Val Glu Ile Thr Leu Tyr Pro Val Asn Asp
  1               5                  10                  15

Thr Ser Cys Thr Arg Thr Thr Thr Gly Leu Ser Glu Ser Ile Leu
             20                  25                  30

Thr Ser Glu Leu Thr Ile Thr Met Asn His Thr Asp Cys Asn Pro Val
         35                  40                  45

Phe Arg Glu Glu Tyr Phe Ser Val Leu Asn Lys Val Ala Thr Ser Gly
     50                  55                  60

Phe Phe Thr Gly Glu Asn Arg Tyr Gln Asn Ile Ser Lys Val Cys Thr
 65                  70                  75                  80

Leu Asn Phe Glu Ile Lys Cys Asn Asn Lys Gly Ser Ser Phe Lys Gln
                 85                  90                  95

Leu Thr Lys Ala Lys Asn Asp Asp Gly Met Met Ser His Ser Glu Thr
            100                 105                 110

Val Thr Leu Ala Gly Asp Cys Leu Ser Ser Val Asp Ile Tyr Ile Leu
        115                 120                 125

Tyr Ser Asn Thr Asn Ala Gln Asp Tyr Glu Thr Asp Thr Ile Ser Tyr
    130                 135                 140

Arg Val Gly Asn Val Leu Asp Asp Asp Ser His Met Pro Gly Ser Cys
145                 150                 155                 160
```

```
Asn Ile His Lys Pro Ile Thr Asn Ser Lys Pro Thr Arg Phe Leu
            165                 170                 175
```

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gcggaattca tgaagtccgt attatactcg                                    30

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gcgctcgagt aaaaagtggg tgggtttgg                                     29

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gcggaattca tgaagtccgt attatacttg                                    30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gcgctcgaga cacgatgtgt cgttaactgg                                    30

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cgcccaccca atggaactag gacgaccact accgg                              35

<210> SEQ ID NO 34
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gcgggatcca tgataaacat aaacataaac acaatac        37

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gcggcggccg cattaatagt tctagtagcg caag        34

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cgcgaattca tgatgatata cggattaata gc        32

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gcggtcgaca ccatcgacac cactcatc        28

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cgcctcgagt cattctcatc ctcatcctc        29

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cgcctcgagg acacacgcta taagttttgc        30

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gcggaattca tgtataaaaa actaataacg ttt                                  33

<210> SEQ ID NO 41
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cgcctcgaga aaatcatatt ttgaataata tgta                                 34

<210> SEQ ID NO 42
<211> LENGTH: 349
<212> TYPE: PRT
<213> ORGANISM: Camelpox virus
<220> FEATURE:
<221> NAME/KEY: MOD_RES
<222> LOCATION: (280)
<223> OTHER INFORMATION: variable amino acid

<400> SEQUENCE: 42

Met Lys Ser Val Leu Tyr Ser Tyr Ile Leu Phe Leu Ser Cys Ile Ile
 1               5                  10                  15

Ile Asn Gly Arg Asp Val Thr Pro Tyr Ala Pro Ser Asn Gly Lys Cys
            20                  25                  30

Lys Asp Asn Glu Tyr Lys Arg His Asn Leu Cys Cys Leu Ser Cys Pro
        35                  40                  45

Pro Gly Thr Tyr Ala Ser Arg Leu Cys Asp Ser Lys Thr Asn Thr Gln
    50                  55                  60

Cys Thr Pro Cys Gly Ser Gly Thr Phe Thr Ser Arg Asn Asn His Leu
65                  70                  75                  80

Pro Ala Cys Leu Ser Cys Asn Gly Arg Cys Asp Ser Asn Gln Val Glu
                85                  90                  95

Thr Arg Ser Cys Asn Thr Thr His Asn Arg Ile Cys Glu Cys Ser Pro
            100                 105                 110

Gly Tyr Tyr Cys Ile Leu Lys Gly Ser Ser Gly Cys Lys Ala Cys Val
        115                 120                 125

Ser Gln Thr Lys Cys Gly Ile Gly Tyr Gly Val Ser Gly His Thr Ser
    130                 135                 140

Ala Gly Asp Val Ile Cys Ser Pro Cys Gly Leu Gly Thr Tyr Ser Arg
145                 150                 155                 160

Thr Val Ser Ser Ala Asp Lys Cys Glu Pro Val Pro Ser Asn Thr Phe
                165                 170                 175

Asn Tyr Ile Asp Val Glu Ile Asn Leu Tyr Pro Val Asn Asp Thr Ser
            180                 185                 190

Cys Thr Arg Thr Thr Thr Gly Ile Ser Glu Ser Ile Ser Thr Ser
        195                 200                 205

Glu Leu Thr Ile Thr Met Asn His Lys Asp Cys Asp Pro Val Phe Arg
    210                 215                 220

Glu Glu Tyr Phe Ser Val Leu Asn Lys Val Ala Thr Ser Gly Phe Phe
225                 230                 235                 240

Thr Gly Glu Asn Arg Tyr Gln Asn Ile Ser Lys Val Cys Thr Leu Asn
                245                 250                 255

Phe Glu Ile Lys Cys Asn Asn Lys Gly Ser Ser Ser Lys Gln Leu Thr
            260                 265                 270

Lys Ala Lys Asn Asp Asp Gly Xaa Met Pro His Ser Glu Thr Val Thr

```
            275                 280                 285
Leu Val Gly Asp Cys Leu Ser Ser Val Asp Ile Tyr Ile Leu Tyr Ser
    290                 295                 300

Asn Thr Asn Thr Gln Asp Tyr Glu Thr Asp Thr Ile Ser Tyr His Ala
305                 310                 315                 320

Gly Asn Val Leu Asp Val Asp Ser His Met Pro Gly Ser Cys Asp Ile
                325                 330                 335

His Pro Leu Ile Thr Asn Ser Lys Pro Thr His Phe Leu
            340                 345

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cgcgtttaaa cggatccatg atgaagatga caccatcata                          40

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cgcctcgaga tctctttcac aatcatttgg tgg                                 33

<210> SEQ ID NO 45
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cgcggtacct caatctcttt cacaatcatt tgg                                 33

<210> SEQ ID NO 46
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cgcggtacct taatctatgc tgttaaagga cagatcac                            38

<210> SEQ ID NO 47
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gcgaagcttt taccatgggt agtatccgga tgcacagaca c                        41
```

<210> SEQ ID NO 48
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gcgaagcttt taccatggac aagaggtctt gttaacagga tac                        43

<210> SEQ ID NO 49
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gcggcggccg cgtagtatcc ggatgcacag acac                                  34

<210> SEQ ID NO 50
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gcggcggccg ccaattcgag tataggaagc agcagtac                              38

<210> SEQ ID NO 51
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gcgctcgaga tctctttcac aatcatttgg tgg                                   33

<210> SEQ ID NO 52
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gcggcggccg catctatgct gttaaaggac agatcac                               37

<210> SEQ ID NO 53
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gcggcggccg cacaagaggt cttgttaaca ggatac                                36

```
<210> SEQ ID NO 54
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gcggcggccg ccactcggac gaccactacc ggtctc                                 36

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gcgctcgagt aaaaagtggg tgggatactg ggaa                                   34

<210> SEQ ID NO 56
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gcggcggccg cacacgatgt gtcgttgacg ggatac                                 36

<210> SEQ ID NO 57
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gcgggtaccg aattcaccat ggagtcatat atattgctat tgc                         43
```